US010398470B2

(12) United States Patent
Olomutzki et al.

(10) Patent No.: US 10,398,470 B2
(45) Date of Patent: Sep. 3, 2019

(54) LEAD EXTRACTION METHODS AND APPARATUS

(71) Applicant: Leadex Cardiac Ltd., Herzliya (IL)

(72) Inventors: Yoav Olomutzki, Kfar Saba (IL); Roey Shafrir, Modi'in (IL)

(73) Assignee: Leadex Cardiac Ltd., Herzliya (IL)

( * ) Notice: Subject to any disclaimer, the term of this patent is extended or adjusted under 35 U.S.C. 154(b) by 188 days.

(21) Appl. No.: 15/233,848

(22) Filed: Aug. 10, 2016

(65) Prior Publication Data

US 2016/0346007 A1 Dec. 1, 2016

Related U.S. Application Data

(63) Continuation of application No. 14/186,428, filed on Feb. 21, 2014, now abandoned, which is a continuation of application No. 14/009,134, filed as application No. PCT/IB2012/000818 on Mar. 30, 2012, now abandoned.

(Continued)

(51) Int. Cl.
A61B 17/34 (2006.01)
A61B 17/3205 (2006.01)
A61N 1/05 (2006.01)
A61B 17/00 (2006.01)

(52) U.S. Cl.
CPC .... A61B 17/3468 (2013.01); A61B 17/32053 (2013.01); A61N 1/05 (2013.01); A61B 2017/00535 (2013.01); A61B 2017/00539 (2013.01)

(58) Field of Classification Search
CPC .......... A61B 17/32053; A61B 17/3468; A61B 2017/00535; A61B 2017/00539; A61N 1/05
See application file for complete search history.

(56) References Cited

U.S. PATENT DOCUMENTS 3,763,864 A 10/1973 Dreman
4,176,662 A 12/1979 Frazer
(Continued)

FOREIGN PATENT DOCUMENTS

JP 63-255168 A 10/1988
JP 2008-155033 A 10/2008

OTHER PUBLICATIONS

International Search Report and Written Opinion for International Patent Application No. PCT/IB2010/000206 dated Apr. 8, 2010.
(Continued)

Primary Examiner — Phong Son H Dang
(74) Attorney, Agent, or Firm — Wolf, Greenfield & Sacks, P.C.

(57) ABSTRACT

An apparatus configured to control a lead extraction tool for assisting in removal of an implanted lead. The apparatus comprises at least one valve configured to control fluid flow to the lead extraction tool. When the at least one valve is open, the at least one valve is configured to allow fluid stored in the apparatus to flow thereby applying, when the apparatus is fluidly coupled to the lead extraction tool, fluid pressure to at least one component of the lead extraction tool. The apparatus further comprises at least one controller configured to control opening and/or closing of the at least one valve.

14 Claims, 40 Drawing Sheets

Related U.S. Application Data

(60) Provisional application No. 61/470,731, filed on Apr. 1, 2011.

(56) References Cited

U.S. PATENT DOCUMENTS

| | | | |
|---|---|---|---|
| 4,429,720 A | 2/1984 | Beck et al. | |
| 4,576,162 A | 3/1986 | McCorkle | |
| 4,848,168 A | 7/1989 | Negishi | |
| 5,013,310 A | 5/1991 | Goode et al. | |
| 5,398,670 A | 3/1995 | Ortiz et al. | |
| 5,556,424 A * | 9/1996 | Hocherl | A61N 1/05 128/897 |
| 5,651,781 A | 7/1997 | Grace | |
| 6,517,498 B1 * | 2/2003 | Burbank | A61B 10/0233 600/564 |
| 8,092,467 B1 * | 1/2012 | Lindstrom | A61B 17/3468 606/108 |
| 9,301,773 B2 | 4/2016 | Olomutzki et al. | |
| 9,339,269 B2 * | 5/2016 | Geistert | A61B 17/0642 |
| 9,649,490 B2 * | 5/2017 | Booker | A61B 17/320016 |
| 10,207,105 B2 * | 2/2019 | Kalmann | A61N 1/056 |
| 2002/0049485 A1 * | 4/2002 | Smits | A61N 1/056 607/122 |
| 2003/0065250 A1 | 4/2003 | Chiel et al. | |
| 2005/0192591 A1 | 9/2005 | Lui et al. | |
| 2006/0184063 A1 | 8/2006 | Miller | |
| 2008/0154296 A1 | 6/2008 | Taylor et al. | |
| 2009/0018468 A1 | 1/2009 | Janssens | |
| 2009/0030436 A1 | 1/2009 | Charles | |
| 2009/0234367 A1 * | 9/2009 | Verma | A61N 1/05 606/129 |
| 2010/0010499 A1 | 1/2010 | Fischer | |
| 2010/0125320 A1 * | 5/2010 | Polkinghorne | A61N 1/05 607/120 |
| 2010/0198229 A1 | 8/2010 | Olomutzki et al. | |
| 2010/0249505 A1 | 9/2010 | Shoham et al. | |
| 2011/0106099 A1 * | 5/2011 | Duffy | A61B 17/32053 606/129 |
| 2012/0029335 A1 * | 2/2012 | Sudam | A61N 1/05 600/374 |
| 2014/0288572 A1 | 9/2014 | Olomutzki et al. | |
| 2016/0022302 A1 | 1/2016 | Olomutzki et al. | |

OTHER PUBLICATIONS

International Preliminary Report on Patentability for International Patent Application No. PCT/IB2010/000206 dated Jul. 28, 2011.
International Search Report and Written Opinion for International Application No. PCT/IB2012/000818, dated Jul. 27, 2012.
International Preliminary Report on Patentability for International Application No. PCT/IB2012/000818 dated Oct. 10, 2013.

\* cited by examiner

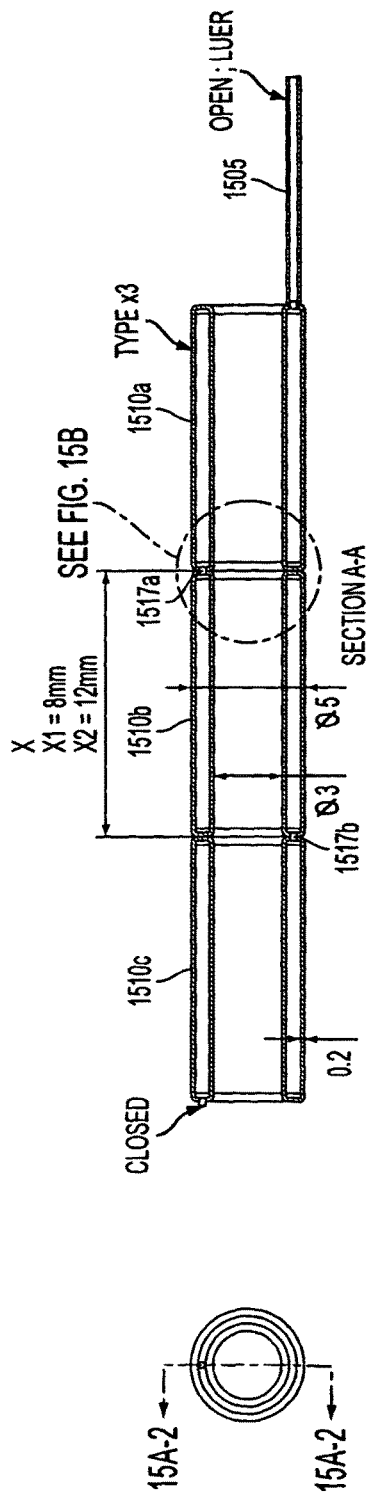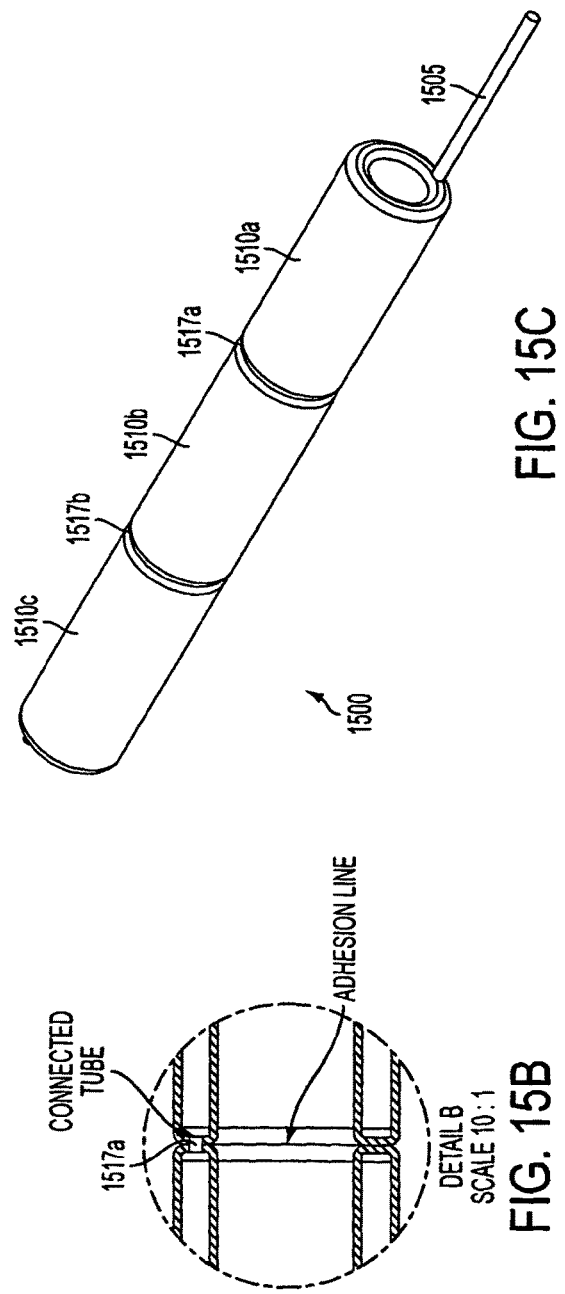

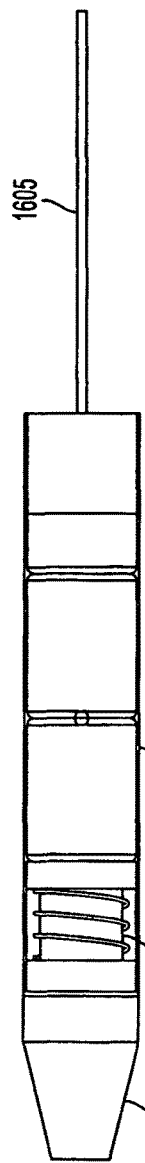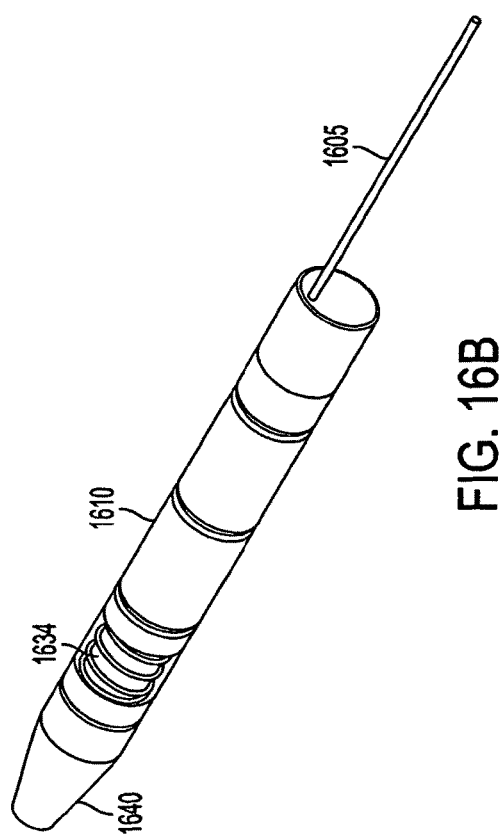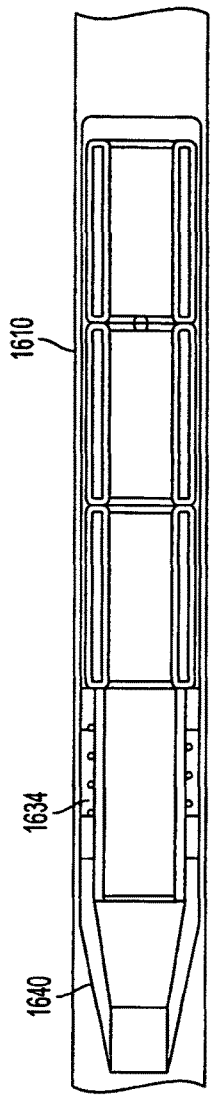

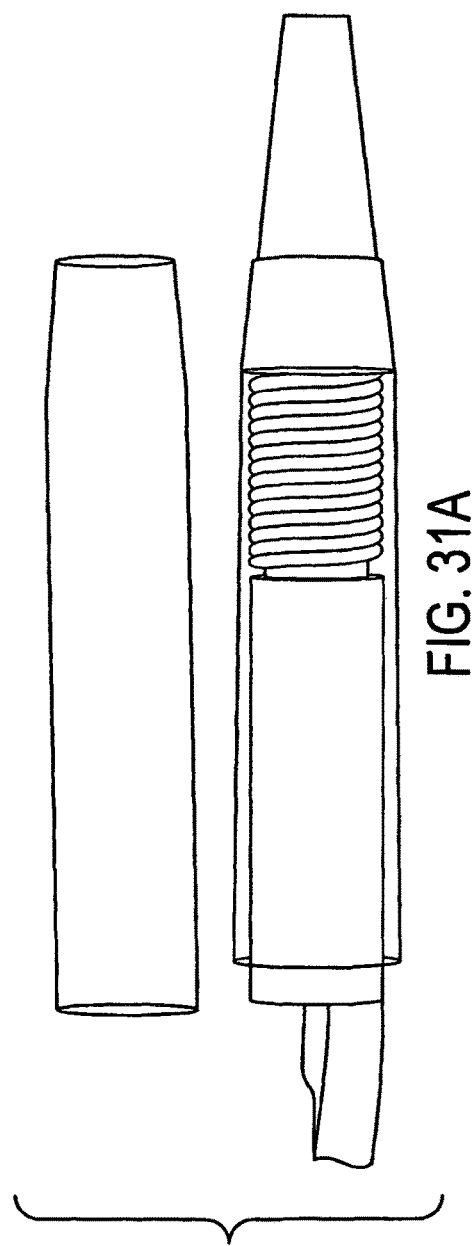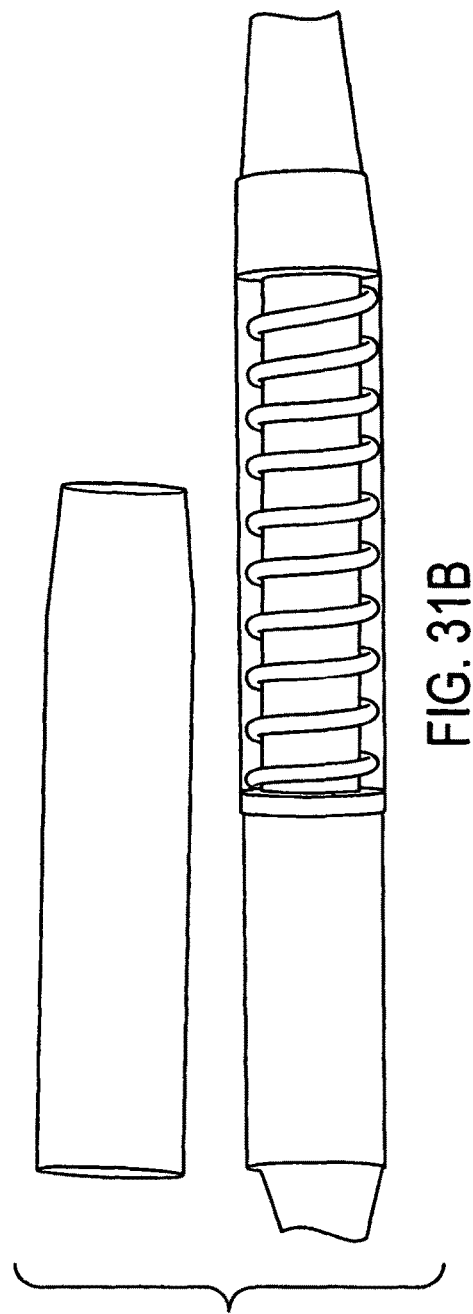
FIG. 31A
FIG. 31B

LEAD EXTRACTION METHODS AND APPARATUS

CROSS-REFERENCE TO RELATED APPLICATIONS

The present application is a continuation of and claims the benefit of U.S. patent application Ser. No. 14/186,428 entitled "LEAD EXTRACTION METHODS AND APPARATUS", filed Feb. 21, 2014, which is a continuation of and claims the benefit of U.S. patent application Ser. No. 14/009,134 entitled "LEAD EXTRACTION METHODS AND APPARATUS", filed Oct. 1, 2013, which is a national stage application under 35 U.S.C. § 371 of International Application Serial No. PCT/IB2012/000818, filed on Mar. 30, 2012, titled "Lead Extraction Methods and Apparatus," which claims the benefit under 35 U.S.C. § 119(e) of U.S. Provisional Application Ser. No. 61/470,731, filed on Apr. 1, 2011, titled "Lead Extraction Methods and Apparatus," each of which is hereby incorporated by reference in its entirety.

BACKGROUND

A number of heart conditions and/or diseases are routinely treated using a pacemaker or implantable cardioverter defibrillator (ICD) that deliver electrical energy to the heart muscle to keep the patient's heart beating at a normal rhythm. Such devices are typically implanted by inserting a thin flexible wire lead into a vein to direct one or more distal electrodes into the atrium and ventricle of the heart. The lead delivers electrical energy to the heart muscle according to a desired rhythm of the heartbeat via the distal electrodes in contact with and/or anchored in the walls of the respective heart chambers. The proximal end of the lead is connected to an energy source that generates the electrical energy provided to the heart via the distal electrode(s).

FIG. 1 illustrates a schematic of one example of a pacemaker implantation. A lead 120 has a terminal connector 130c at one end and distal electrodes 130a and 130b at the other end. The lead is inserted into the right or left subclavian vein and maneuvered such that distal electrode 130a contacts the atrium wall and/or distal electrode 130b contacts the ventricle wall of the heart. The proximal end of the lead (terminal connector) is connected to an energy source that provides electrical energy to the heart, via the lead 120, at a desired rhythm or pattern, which itself undergoes a subcutaneous or submuscular implantation procedure. It should be appreciated that FIG. 1 is not intended to be an accurate depiction of a pacing system, but is merely used to demonstrate the idea of device implantation. For example, the two distal electrodes are illustrated as merging into the same lead, however, multiple electrodes may each have there own independent lead connected to the energy source. Typical pacing systems may include one, two, three, four or more leads and associated electrodes. Moreover, in the dual electrode system shown in FIG. 1, one electrode may be referred to as the distal electrode and the other the proximal electrode (e.g., the tip and ring electrodes used for bipolar stimulation).

Subsequent to implant, lead 120 may need to be extracted from the body for any number of reasons. Infection caused by the pacing system (e.g., infection resulting from the implanted leads or the pacing generator pocket) is the leading reason for a physician to determine that, for the patient's safety, the lead(s) should be extracted from the body. In addition, physical damage to the lead may require lead extraction. For example, fracturing of the lead or damage to the insulation surrounding the lead may cause the device to operate non-optimally, to be altogether non-functional and/or present a risk to the patient, and therefore may require the lead to be extracted and optionally replaced. A lead left in the body from a previously removed device may need to be removed due to interference with a new lead and/or pacing device. For example, an abandoned lead may occupy intravenous space preventing a new lead from being inserted, thus requiring the abandoned lead to be removed.

Lead interaction with the body may also require the lead to be extracted. For example, excessive scar tissue at the tip of the lead may render the lead non-functional and/or may require the device to provide more energy than the device was designed to deliver. Venous obstruction by the lead causing interruption of the blood flow, interference of the lead with the circulatory system or other implanted devices, and/or pain at the site of implant all may recommend extraction of the lead. Numerous other complications may arise that cause a physician to determine that lead extraction is required for the patient's comfort, safety and/or livelihood. For example, a physician may want to replace a lead from a potentially dangerous recalled device or update an older device with a new device to exploit new technological advances.

Many conventional lead extraction devices operate by threading an expandable ("locking") wire through the lumen of the lead. Standard pacemaker leads are formed from a coiled wire having a hollow center (lumen) along the axis of the lead. The lead lumen may be used to assist in extracting the lead from the body. Such lead extraction devices typically operate by having a guide wire with an outer diameter less than the inner diameter of the lead threaded through the lumen until it reaches the distal end (e.g., the location in which the lead is anchored into the ventricle or atrium wall of the heart).

The guide wire may be provided with a distal portion that can be expanded to engage and grip the internal wire coil of the lead. For example, the distal end of the guide wire may include a coil of wire that can be unwound from the proximal side of the guide wire once the guide wire has reached the distal end (e.g., the implantation end) of the lead. As the wire unwinds, it tangles with the internal wire coil of the lead to anchor the distal end of the guide wire. The guide wire may then be pulled out, extracting the lead along with it.

However, lead extraction may be complicated by tissue adhering to the outer surface of the lead. For example, after the lead has been implanted, scar tissue may form around the lead at any number of different sites (e.g., the insertion point of the lead into the vein or at any location along the vein and/or heart wall) making it difficult for a surgeon to extract the lead without tearing the surrounding tissue. Moreover, if more than one lead is present in the vein, the leads can become attached to one another creating a relatively complicated extraction procedure that is often problematic using conventional lead extraction devices. Lead extraction devices that utilize the internal lumen of the lead for extraction do not address the problem of fibrous tissue attached to the external portion of the lead and may therefore be rendered ineffective, or are used with significant risk of tearing critical internal blood vessels and causing dangerous, and sometimes fatal, damage to the patient should the lead be extracted using excessive force.

To address issues related to tissue adhering to the outside circumference of the lead, conventional methods and devices have used various relatively rudimentary manual devices that cut the surrounding tissue with a knife or edged implement operated by a surgeon and/or utilize laser or diathermic devices that provide laser or electrical energy to cut the surrounding tissue to release the lead for extraction. For example, a hollow sheath having a cutting portion on the distal end may be threaded over the lead. A surgeon may then manually force the sheath forward so that the cutting portion engages the attached tissue and cuts the tissue away from the lead. The surgeon may also manually rotate the sheath to facilitate cutting and or use a trigger gun that attaches to the sheath and that rotates the sheath when the trigger is engaged. In some embodiments, laser or diathermic devices are affixed to the cutting portion of the lead to ablate the tissue to assist in separating surrounding tissue from the lead.

SUMMARY

In some embodiments, an apparatus configured to control a lead extraction tool for assisting in removal of an implanted lead is disclosed. The apparatus comprises at least one valve configured to control fluid flow to the lead extraction tool, wherein when the at least one valve is open, the at least one valve is configured to allow fluid stored in the apparatus to flow thereby applying, when the apparatus is fluidly coupled to the lead extraction tool, fluid pressure to at least one component of the lead extraction too, and at least one controller configured to control opening and/or closing of the at least one valve.

The foregoing is a non-limiting summary of the invention, which is defined by the attached claims.

BRIEF DESCRIPTION OF THE DRAWINGS

FIGS. 15A-1, 15A-2, 15B, and 15C illustrate different views of a chain of balloons capable of both anchoring and advancing a lead extraction device, in accordance with some embodiments of the present invention;

FIGS. 16A, 16B, and 16C illustrate views of a lead extraction device incorporating at least some anchoring/advancing techniques discussed in connections with FIGS. 13-15, in accordance with some embodiments of the present invention;

FIGS. 18A-1 and 18A-2 illustrate a normal and cross-sectional view of an expansion portion for a lead extraction device in the deflated state, in accordance with some embodiments of the present invention;

FIGS. 18B-1 and 18B-2 illustrate a normal and cross-sectional view of an expansion portion for a lead extraction device in the inflated state, in accordance with some embodiments of the present invention;

FIGS. 31A-B illustrate a lead extraction device comprising a tube configured to cover a spring on the lead extraction device, in accordance with some embodiments of the present invention.

DETAILED DESCRIPTION

Figure 1:
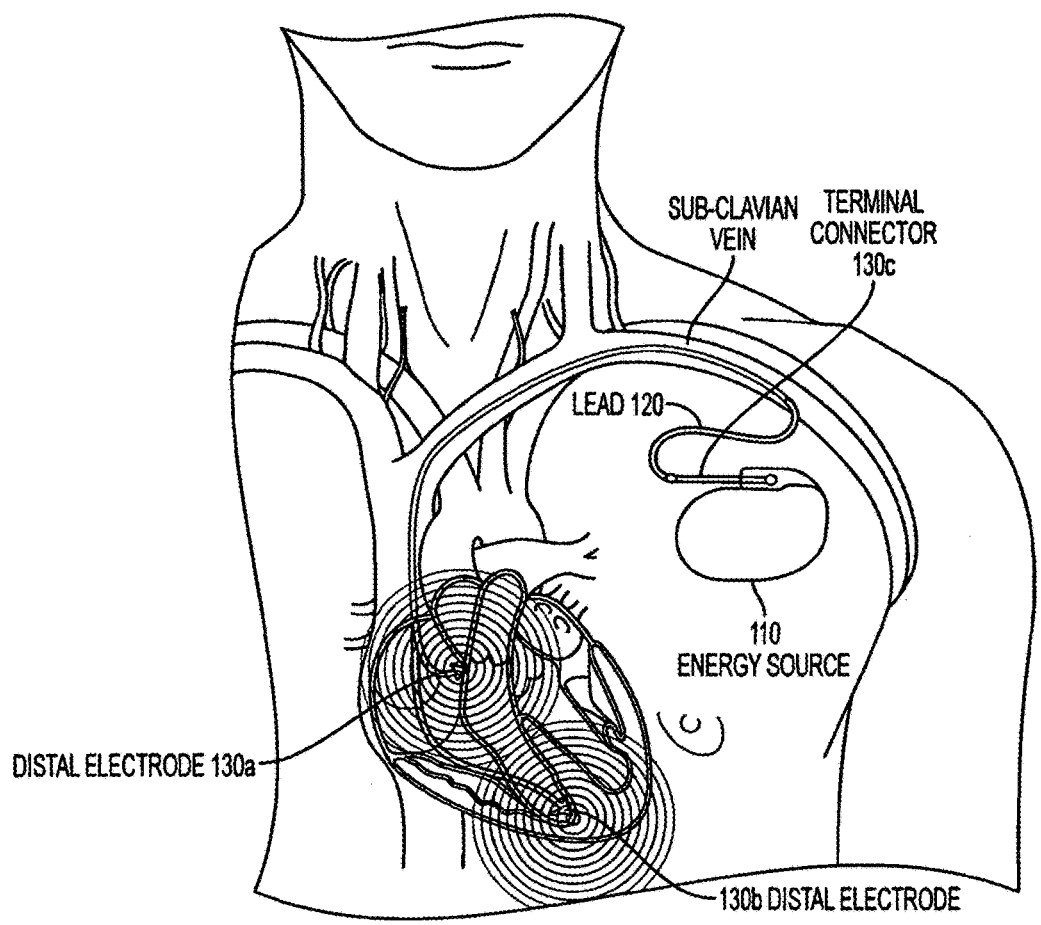
FIG. 1 illustrates an implanted pacing system.

As discussed above, most conventional lead extraction techniques rely on either rudimentary manual cutting devices or laser or diathermic devices that ablate surrounding tissue using laser or electrical energy. Drawbacks of conventional manual cutting devices include that the manual devices are often awkward and difficult to operate, placing a relatively heavy burden reliance on the dexterity of the physician and increasing the risk of complicating the procedure. In particular, operating the cutting blade and advancing the device forward to completely release the lead may be considerably difficult, often leading to excessive tissue damage, further complications and/or increasingly invasive surgical procedures to extract the lead. Laser or diathermic devices may provide some improvements with respect to the complexity and success rate of lead extraction over conventional manual extraction devices, however, the equipment is relatively expensive and may not be available to surgeons performing such procedures.

Applicant has appreciated that utilizing pressure changes to semi-automate or fully-automate at least part of the lead extraction process may result in simpler, safer and more effective lead extraction procedures. For example, one or more hydraulic and/or pneumatic techniques may be used to advance a lead extraction device along a lead. According to some embodiments, fluid pressure changes are used to inflate/deflate one or more balloons, tubes or other components, to anchor and/or advance the device over the lead and/or to cut/separate tissue from the lead. As used herein, the term inflate describes the operation of increasing fluid pressure and the term deflate describes the operation of decreasing fluid pressure. The term fluid is used herein to describe gases, liquids and some solids (e.g., foams or other solids that can be used to effect pressure changes). According to some embodiments, anchoring, advancing, and cutting is achieved utilizing fluid pressure techniques.

In some embodiments, a control unit may be used to partially or fully automate the lead extraction process by controlling the advancement of a lead extraction device along the lead. The control unit may be configured to generate changes in fluid pressure, which in turn may be used to inflate/deflate one or more balloons, tubes, or other components of the lead extraction device to anchor and/or advance the device over the lead and/or to cut/separate tissue from the lead. In some embodiments, the control unit may be configured to generate fluid pressure changes using one or more accumulators (e.g., compressed-gas accumulator, spring-based accumulator, etc.) and/or any of numerous other components for regulating pressure (e.g., pressure regulators, pressure valves, etc.). In some embodiments, the control unit may be a hand-held device.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments below may be used alone or in any combination, and are not limited to the combinations explicitly described herein.

Figure 2:
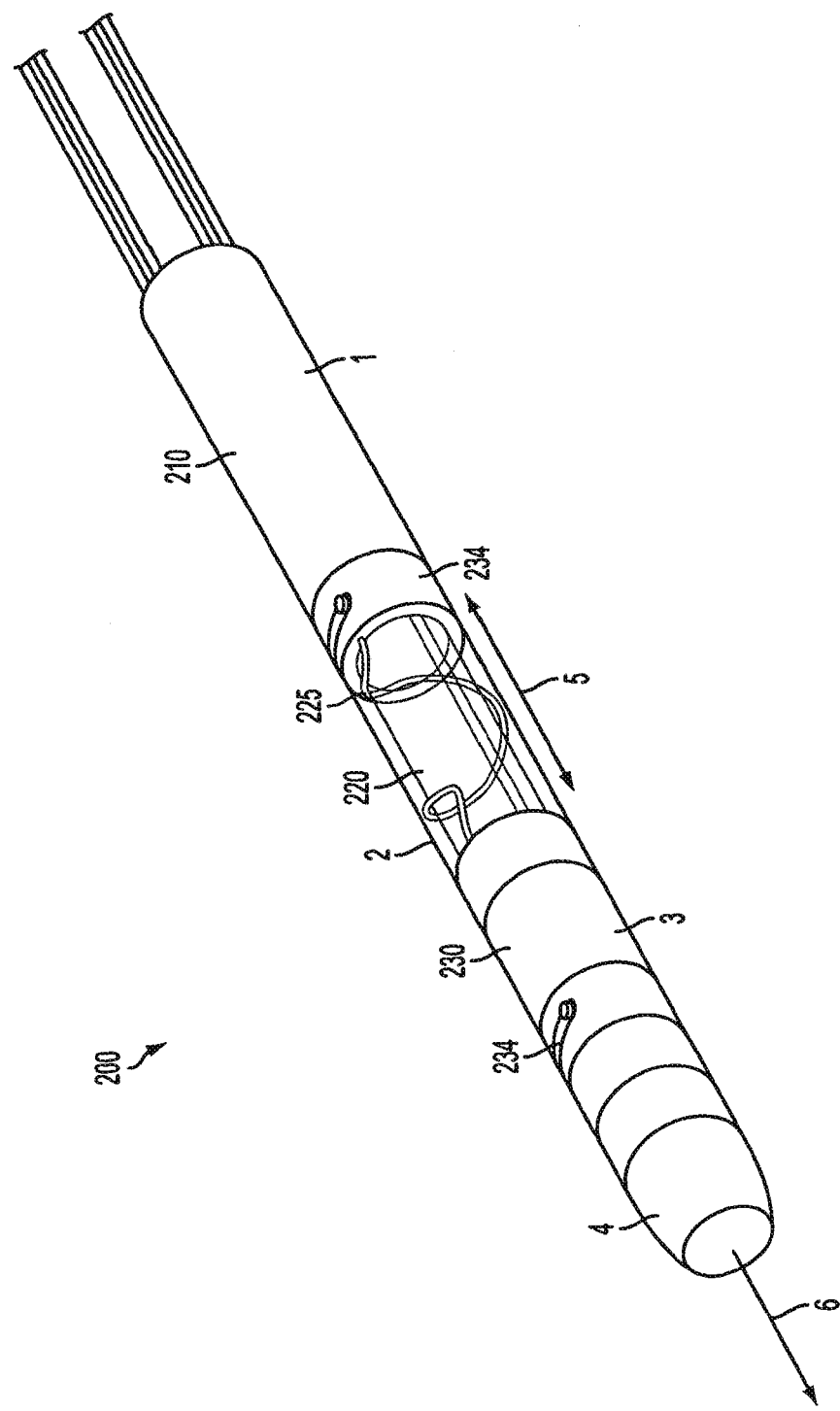
FIG. 2 illustrates a lead extraction device to assist in lead removal, in accordance with some embodiments of the present invention.

FIG. 2 illustrates a lead extraction device in accordance with some embodiments of the present invention. Device 200 comprises a body 5 having a hollow central axis that is at least wide enough to accommodate a heart lead. The body includes a proximal portion 1, an expansion portion 2, a distal portion 3 and a cutting portion 4. Cutting portion 4 may be positioned at a distal end of the device (e.g., at one end of distal portion 3) and may be, for example, a circular blade having an opening designed to accommodate a lead and capable of cutting tissue that has grown on the lead as the device is advanced along the lead in the direction indicated by arrow 6.

In some embodiments, cutting portion 4 rotates as the device advances along the lead to facilitate separating the lead from any tissue that has grown on, or otherwise adhered to the lead, and or two separate two leads from one another. In other embodiments, the blade does not rotate and tissue separation is performed by the cutting portion being advanced along the lead, as discussed in further detail below. The cutting portion may rotate and advance simultaneously or rotation and advancement may be two separate and independent motions. The rotation of the cutting portion may be in a single direction (e.g., clockwise rotation) or may rotate both clockwise and counterclockwise in alternation. The cutting portion may fully rotate or may affect only partial rotation, as the aspects of the invention are not limited for use with any particular cutting mechanism.

Proximal portion 1 may be located at the opposite end of the device from the cutting blade and may contain one or more anchoring balloons 210 adapted to grip the lead when inflated. In some embodiments, the anchoring balloon is torus shaped such that when deflated a lead can pass through the center of the torus unimpeded and when inflated the balloon constricts and grips the lead to anchor the device, as discussed in further detail below. The term "balloon" refers herein to any structure or combination of structures, having one or more portions that vary under fluid pressure. For example, a balloon may include structure(s) having one or more portions capable of being inflated and/or deflated using forced fluid (e.g., forced air, liquid or solid such as foam). A balloon can be a single component or formed from multiple components depending on what effect is desired upon inflating/deflating the balloon (e.g., elongation, constriction, anchoring, etc.).

Figure 3A:
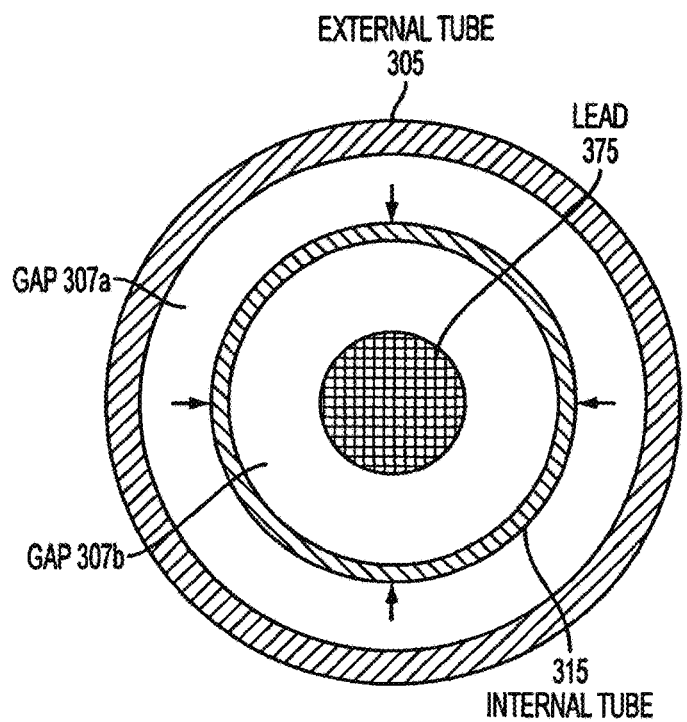
FIGS. 3A and 3B illustrate an example of one type of anchoring balloon in the deflated and inflated states, respectively, in accordance with some embodiments of the present invention.
Figure 3B:
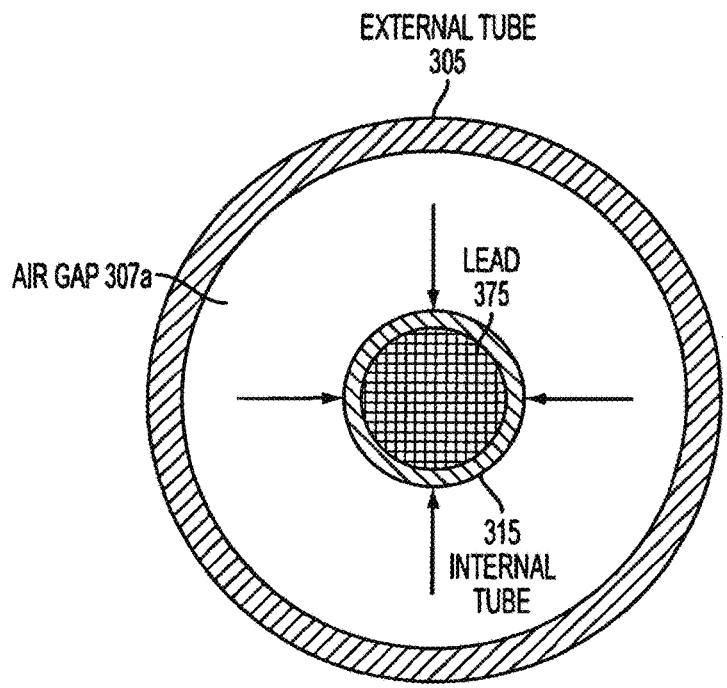

FIGS. 3A and 3B illustrate a cross-section of an anchoring component (e.g., an anchoring balloon) in both the deflated and inflated states, respectively, in accordance with some embodiments of the present invention. In FIGS. 3A and 3B, the anchoring component includes a balloon comprised of an outer tube 305 formed from a relatively rigid material (e.g., a steel, silicone or polymer tube) and an inner tube formed from a relatively elastic material (e.g., silicone, nylon, polymer or other materials by which medical balloons and/or tubing are formed).

In the deflated state illustrated in FIG. 3A, a gap 307a may exists between the outer and inner tube whereby the pressure within the gap permits the inner tube to relax such that there is a gap 307b between the inner tube 315 and the lead 375 and/or sufficient space or lack of resistance between inner tube 315 and lead 375 such that the anchoring component is capable of movement along the length of the lead. Inflating the anchoring component may include forcing fluid (e.g., air, liquid, etc.) into gap 307a causing increased pressure to be exerted on the inner tube. Because the outer tube is relatively rigid and resistant to expansion, the increased pressure causes the inner tube to depress inwards to grip the lead and fix the anchoring component relative to the lead, as illustrated in FIG. 3B. In particular, gap 307 expands under the increased pressure caused by fluid inflating pressing the inner tube towards the lead and causing gap 307b to decrease and/or be entirely removed as the inner tube constricts around the lead.

Figure 3C:
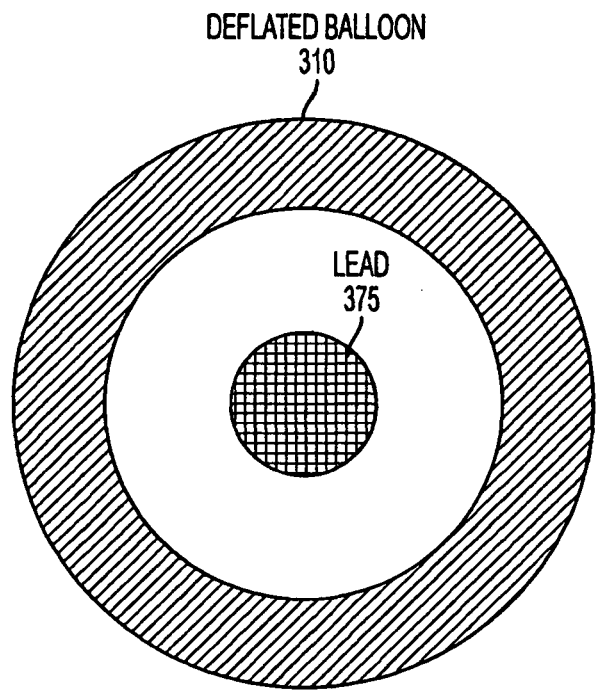
FIGS. 3C and 3D illustrate an example of one type of anchoring balloon in the deflated and inflated states, respectively, in accordance with some embodiments of the present invention.
Figure 3D:
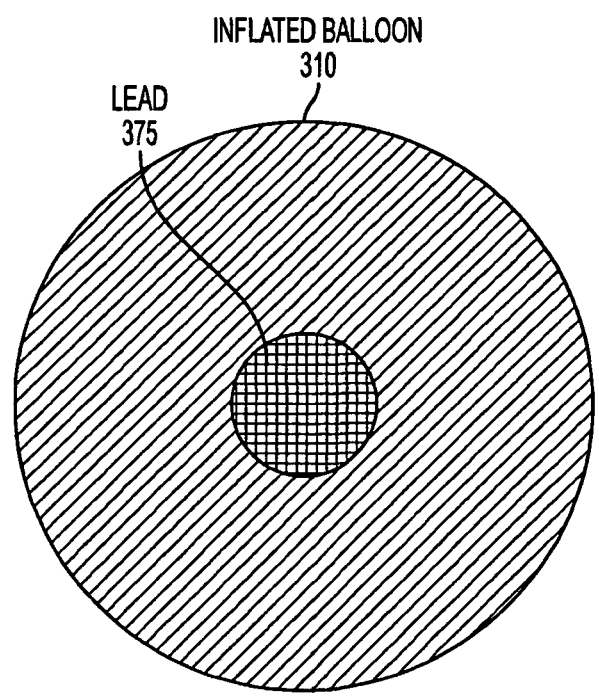

FIGS. 3C and 3D illustrate a cross-section of an anchoring balloon in both the deflated and inflated stages, respectively, in accordance with alternative embodiments. Balloon 310 may be a torus shaped balloon that forms a central hole that, when the balloon is deflated, has a diameter that can accommodate the heart lead and allow relative movement between the lead and the balloon. As illustrated in FIG. 3C, balloon 310 is deflated and lead 375 passes through the center of the balloon relatively unimpeded as the inner wall of the balloon does not grip lead, thus allowing the balloon to slide up or down the lead. In FIG. 3D, balloon 310 has been inflated such that the inner wall of the balloon grips the lead and the friction therebetween prevents motion of the balloon relative to the lead. That is, inflation causes fluid to fill the balloon, simultaneously reducing the size of the center hole until the inner wall grips the lead. The anchoring balloons need not be designed to accommodate the lead through a center of the balloon. For example, a balloon may be disposed over, under or to the side of a lead such that when the balloon is inflated, the balloon applies pressure to the lead such that the balloon resists relative movement between the lead and some portion of the lead extraction device.

It should be appreciated that the expansion of balloon 310 in an outward direction may be substantially prevented, for example, by providing the balloon inside a relatively rigid tube (e.g., the body or outer tube of the lead extraction device) such that expansion of the balloon outward is prevented and inflation results primarily or substantially in inward constriction of the center hole. The relatively rigid tube may be formed from any material such as metal, plastic, polymer, silicone or any other suitable material. Outward expansion of the balloon may be prevented in other ways, as the aspects of the invention are not limited in this respect.

Figure 28A:
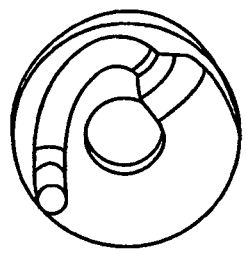
FIGS. 28A-C illustrate views of a spiral balloon, in accordance with some embodiments of the present invention.
Figure 28B:
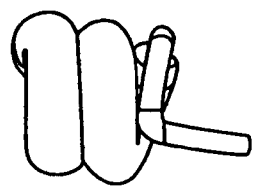
Figure 28C:
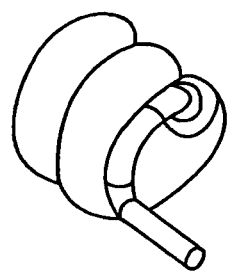

While the balloon illustrated in FIGS. 3C and 3D is toroidal in shape, it should be appreciated that the anchoring balloon may be of any shape capable of gripping and releasing a lead. In some embodiments, for example, the anchoring balloon may be spiral in shape as illustrated in FIGS. 28A, 28B, and 28C. The spiral shape may be a spring-like shape. The lead may be threaded through the inside of the spiral. Such a spiral-shaped balloon may inflate inward and, when sufficiently inflated, may grip the lead and the friction between the inflated spiral balloon and the lead may prevent motion of the balloon relative to the lead. Other methods of achieving anchoring using pressure changes may be used as well, as the aspects of the invention are not limited in this respect. It should be appreciated that the cross-sections of the anchoring balloons in FIGS. 3A-3D are merely schematic to illustrate principles of anchoring via balloon inflation. The dimensions illustrated are not meant to depict actual absolute or relative dimensions.

Referring back to FIG. 2, expansion portion 2 includes a spring mechanism 225 and an elongation component 220 (e.g., one or more elongation balloons). Spring mechanism 225 connects the proximal portion with the distal portion and an elongation balloon 220 is arranged to stretch the spring when inflated and allow the spring to return to repose when deflated. The elongation component may be formed from and inner tube and an outer tube, both of which may be relatively flexible. The inner tube and the outer tube may be connected to each other at each end (e.g., at the end where the expansion portion connects to the proximal portion and at the end where the expansion portion connects to the distal portion).

Inflating the space between the inner tube and the outer tube causes the elongation component 220 to expand, thereby stretching the spring and increasing the distance between the proximal portion and distal. When the space is deflated, the spring relaxes and returns to repose, thereby reducing the distance between the distal and the proximal portions of the device. Spring mechanism 225 may be any type of component such as a standard spring or an accordion type material that can be elongated under fluid pressure.

Distal portion 3 may include one or more distal anchoring balloons (or any other type of anchoring mechanism) arranged to grip the lead at the distal end of the device. The one or more distal anchoring balloons may be similar in construction and operation to the anchoring balloons described in connection with FIGS. 3A-3D, FIGS. 28A-28C, or may be any other type of component capable of gripping and releasing the lead under fluid pressure as desired, as the aspects of the invention are not limited in this respect. Device 200 may also include a rotation component 234 coupled to the cutting portion to cause the cutting portion to rotate as the device advance forward along the lead. In FIG. 2, rotation component 234 has a member on both the proximal and distal end of the device to effect rotation and may use a slot and pin mechanism, as discussed in further detail below. Other types of rotation mechanisms may also be used (some embodiments of which are also discussed below), as the aspects of the invention are not limited for use with any particular type of rotation component.

FIGS. 4A-4F illustrates the internal components of a lead extraction device (e.g., the internal components of lead extraction device 200 illustrated in FIG. 2) at each of a number of stages of an extraction operation cycle that advances the device over the lead and separates the lead from any attached tissue that may prevent the removal of the lead, according to some embodiments. Similar to device 200, device 400 includes a proximal anchor balloon 410, an expansion balloon 420, a distal anchoring balloon 430 and a spring 425 that connects the distal and proximal portions of the device. Device 400 is shown inserted over a lead 495, for example, by a surgeon that threads the exposed end of the lead through the central axis of the sheath.

Figure 4A:
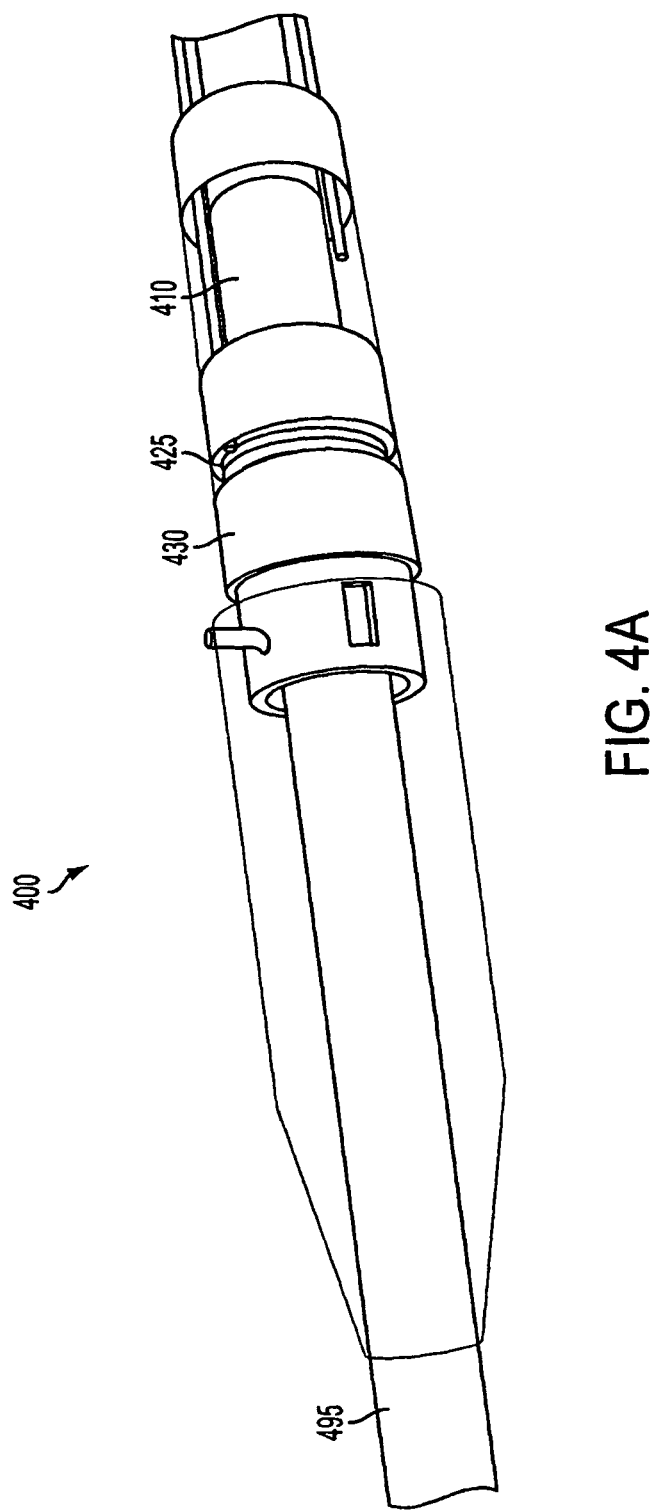
FIGS. 4A-4F illustrate a number of stages of an operation cycle of a lead extraction device, in accordance with some embodiments of the present invention.

FIG. 4A illustrates a first stage of an operation cycle of the lead extraction device after the device has been placed on the lead. In the first stage, all of the balloons may be deflated.

In particular, anchoring balloons 410 and 430 are deflated such that the device is free to slide along the lead (i.e., the lead can pass through the center of the sheath relatively unimpeded by either anchoring balloons. This stage allows the surgeon to thread the lead through the center of the sheath and position the device for extraction of the lead. In addition, the expansion balloon 420 may also be deflated such that spring 425 is in repose and the distal and proximal portion are as close together as the spring will allow. From this stage, the device is ready to begin extracting the lead.

Figure 4B:
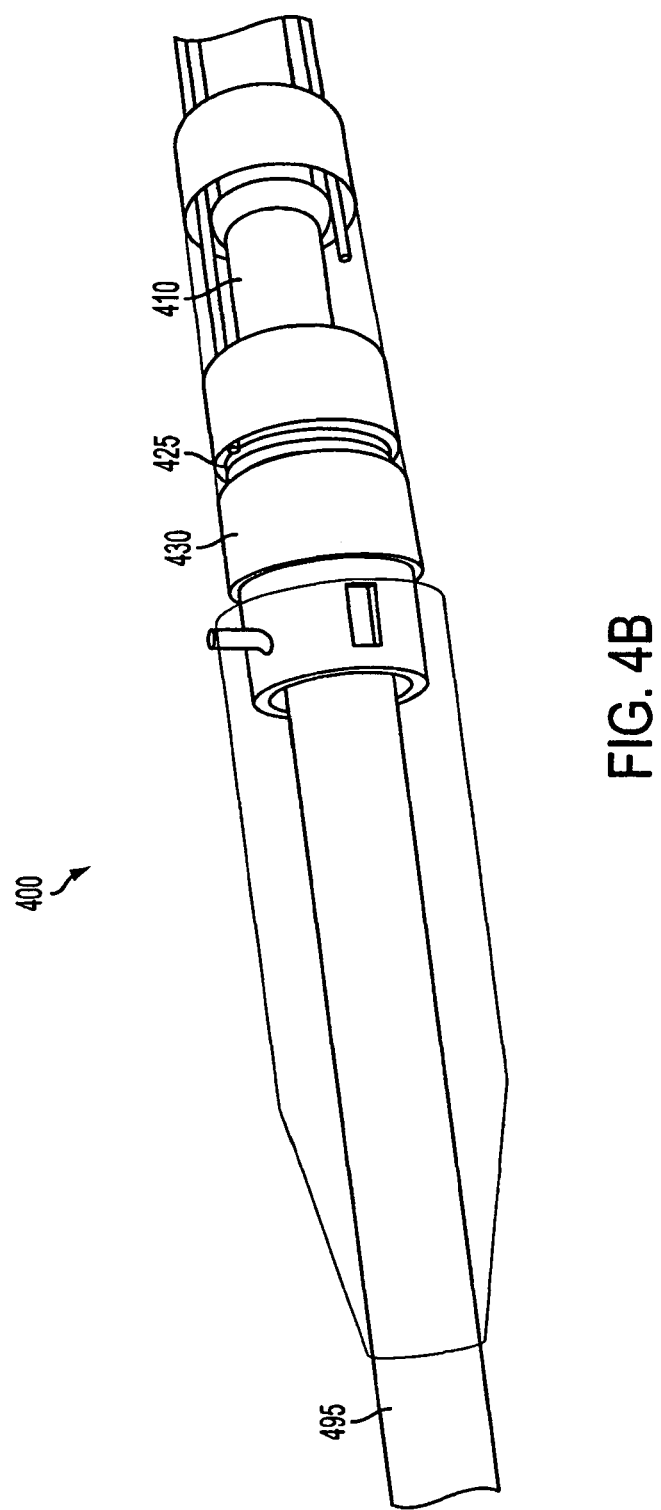

FIG. 4B illustrates a second stage of the operation cycle of the lead extraction device. In the second stage, the proximal anchoring balloon 410 is inflated such that the balloon grips the lead and anchors the proximal portion of the device such that motion of the proximal portion relative to the lead is prevented. For example, the proximal anchoring balloon 410 may transition from deflated (e.g., as shown in FIG. 3A) to inflated (e.g., as shown in FIG. 3B) such that the inner tube is pressed inward to grip the lead. Alternatively, proximal anchoring balloon 410 may be implemented as the torus shaped balloon described in connection with FIGS. 3C and 3D, such that inflation causes the center hole to constrict around the threaded lead.

Figure 4C:
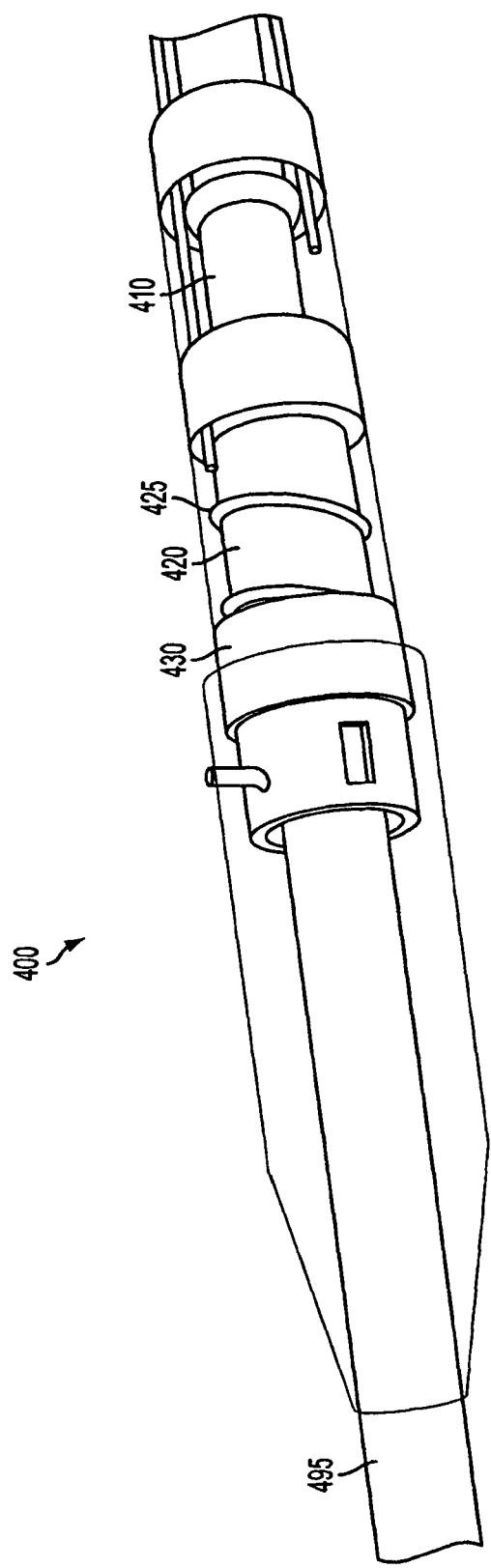

FIG. 4C illustrates a third stage of the operation cycle that advances the distal portion of the device forward along the lead, separating tissue that may be attached to the lead. In this third stage, the elongation balloon 420 is inflated to stretch spring 425. Since the proximal portion of the device is anchored by inflated anchoring balloon 410, the spring forces the distal portion forward along the lead as the spring is stretched by elongation balloon 420. The forward force on the distal portion causes the cutting portion to advance along the lead and cut tissue attached to the lead to prepare the lead for extraction. In some embodiments, the forward force also rotates the cutting portion to facilitate separating the tissue from the lead, as discussed in further detail below.

Figure 4D:
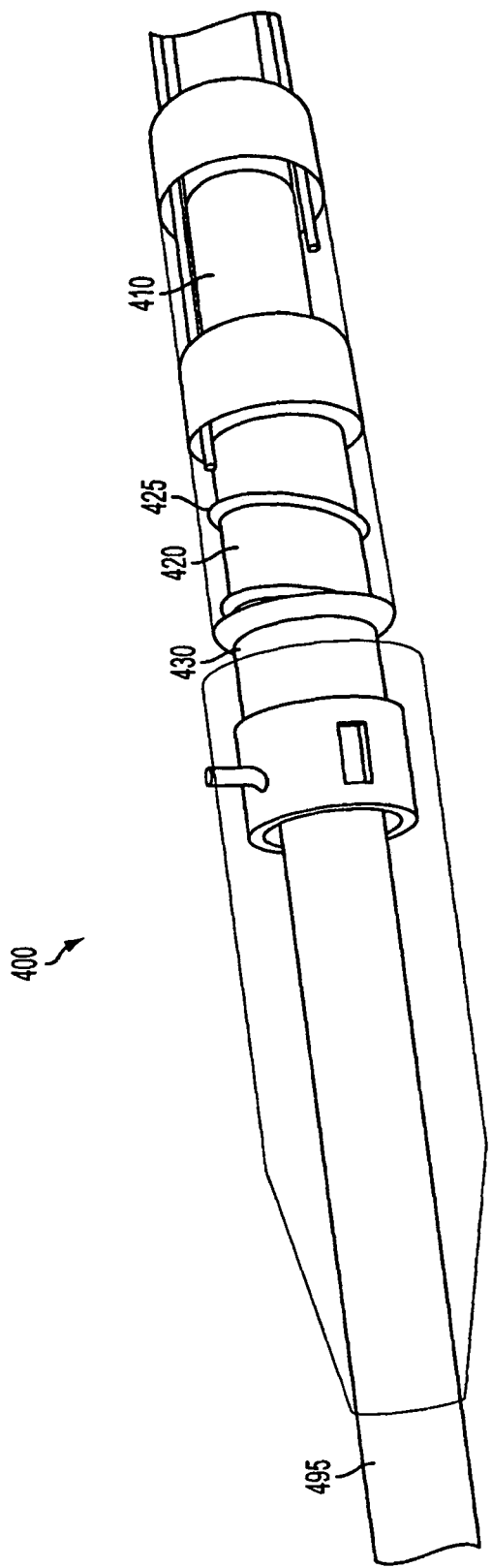

FIG. 4D illustrates a fourth stage of the operation cycle that anchors the distal portion of the device to the lead. After the distal portion has been advanced along the lead, the distal anchoring balloon 430 may be inflated to grip the lead. Anchoring balloon 430 may operate in a same or similar manner as the proximal balloon 410 described above. At this stage, both the proximal and distal portions of the device are anchored to the lead and the spring 425 is stretched by the inflated elongation balloon 420. It should be appreciated that anchoring balloon 430 may include an inflation tube or other inflation mechanism, although no such mechanism is illustrated in FIGS. 4A-4F. Alternatively, anchoring balloon 430 may be replaced with an anchoring component that applies a substantially constant resistance to movement relative to the lead such that inflation/deflation of the distal anchoring component is not necessary, some embodiments of which are discussed in further detail below.

Figure 4E:
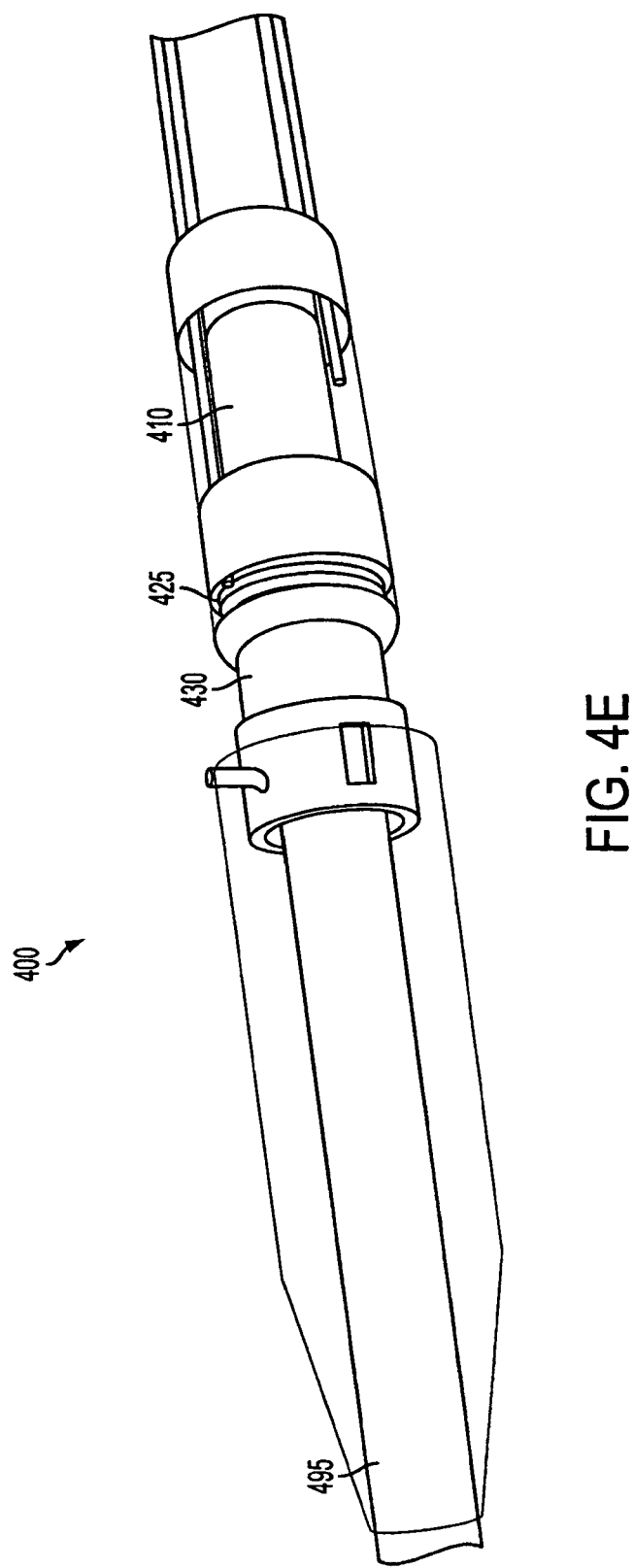
Figure 4F:
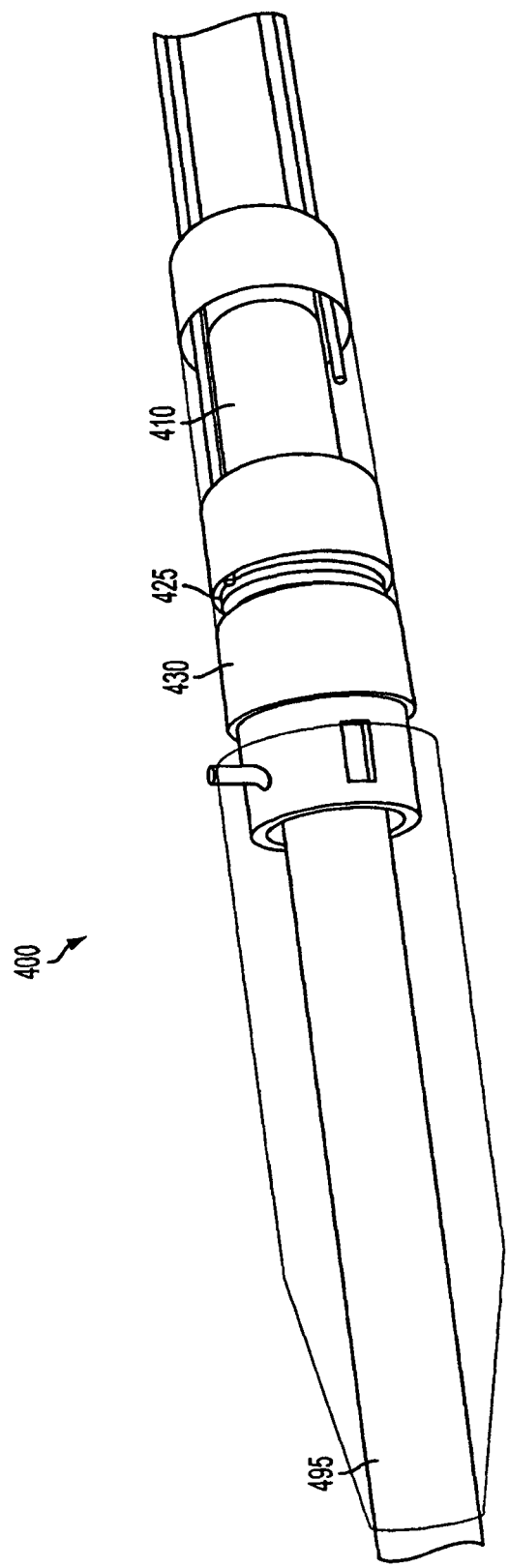

FIG. 4E illustrates a fifth stage of the operation cycle wherein the elongation balloon 420 is deflated causing the spring 425 to tend to relax back to repose. Subsequent to or simultaneously with deflating the elongation balloon 420, proximal anchoring balloon 410 is also deflated. Because the distal anchoring balloon 430 is inflated, the force of the contracting spring as it returns to repose pulls the proximal portion of the device (now released due to the deflation of the proximal anchoring balloon 410) forwards to advance the proximal portion of the device along the lead. The distal anchoring balloon may then be deflated to return the device to the first stage. That is, all balloons may be deflated and the device returns to its initial configuration but has been advanced along the lead, separating (or at least partially cutting/separating) tissue that the cutting portion may have encountered during the incremental advancement of the operation cycle (see e.g., FIG. 4F).

The stages may be repeated to continue to advance the device forward until the device has advanced as far as it needs to advance in order to release the lead so that it can be pulled from the body. It should be appreciated that the various stages need not be performed sequentially and portions of the stages or entire stages may be performed simultaneously and/or may overlap in time, as the aspects of the invention are not limited for use with any particular timing scheme.

The lead extraction devices described above embody a number of general concepts that facilitate advancing a lead extraction device along a lead while separating tissue that has attached to the lead and/or separating the lead from another lead to which is has adhered. For example, the lead extraction devices described above illustrate examples of how a lead extraction device can be internally advanced using applied pressure changes, including using applied pressure changes to anchor, advance, and/or cut. It should be appreciated that anchoring, advancing and cutting can be implemented in a variety of different ways, some embodiments of which are described in further detail below. It should be further appreciated that implementations embodying the concepts of anchoring, advancing, and cutting may be used alone or in any combination, as the aspects of the invention are not limited to the specific combinations specifically illustrated herein.

In some embodiments, the distal anchoring component is formed from a constant friction component, rather than an inflatable/deflatable anchoring component (e.g., the inflatable/deflatable anchoring balloons illustrated in FIGS. 3A-3D). For example, the distal anchoring component may provide a constant friction to the lead that is greater than the resistance of the proximal anchoring component on the lead when it is not engaged (e.g., deflated) and less than the resistance of proximal anchoring component on the lead when it is engaged (e.g., when inflated), as discussed in further detail below.

Figure 5:
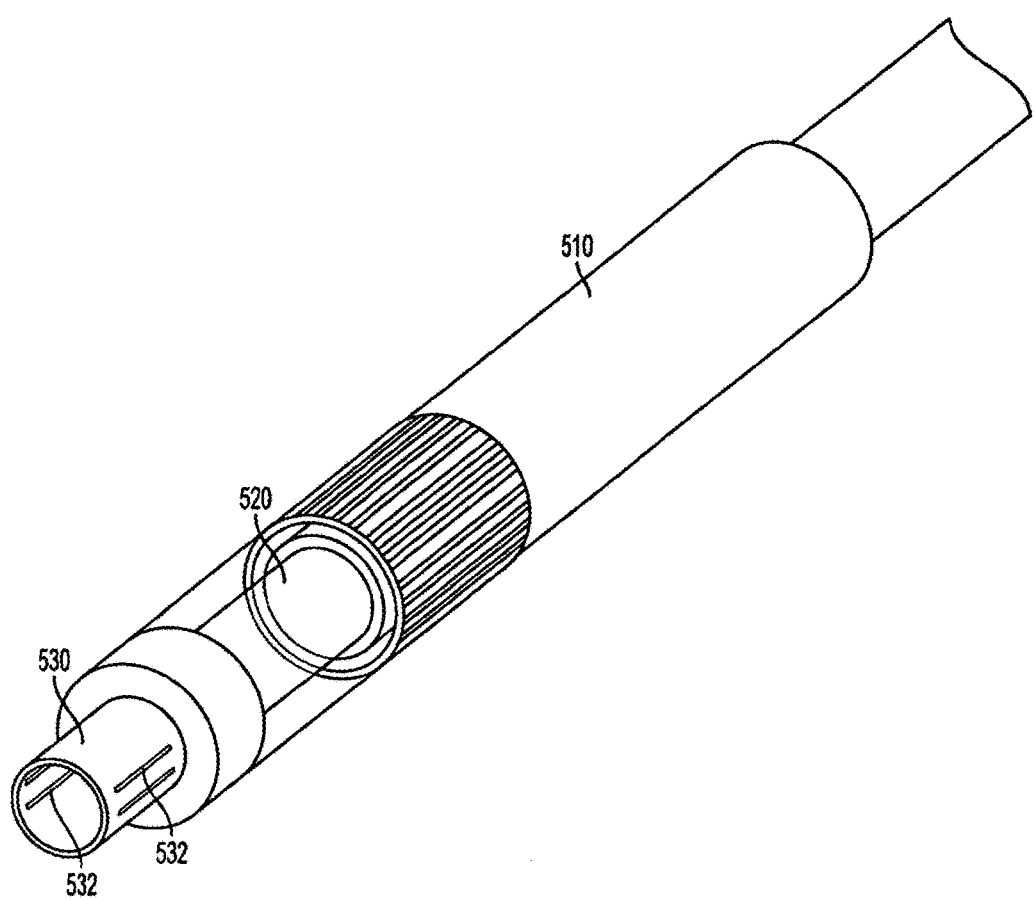
FIG. 5 illustrates a portion of a lead extraction device comprising a distal anchoring component having a constant friction portion, in accordance with some embodiments of the present invention.

FIG. 5 illustrates a distal anchoring component having a constant friction portion, in accordance with some embodiments of the present invention. Proximal anchoring component may be any of the anchoring components described herein capable of anchoring and releasing a lead as desired due to fluid pressure changes. Similarly, expansion component 520 may include any of the mechanisms described above for elongating the distance between the proximal and distal portions of the lead extraction device (e.g., one or more elongation balloons). Distal anchoring component 530 may be a constant friction component that applies a substantially constant friction on the lead.

Distal anchoring component 530 may be a relatively rigid tube having a portion that is bent inwards to contact the lead to apply a constant friction. For example, the rigid tube may have one or more perforated tabs 532 that can be pressed inward to pinch the lead to provide a desired resistance against motion along the lead. In an alternative embodiment, the constant friction component may be formed by twisting a spring that contacts the lead at desired locations and pressure to apply a substantially constant friction to the lead.

As discussed above, the distal anchoring component may have a substantially constant resistance that is greater than the resistance of the proximal anchoring component when the proximal anchoring component is not engaged and less than the resistance of the proximal anchoring component when the proximal anchoring component is engaged. Thus configured, when the proximal anchoring component is engaged with the lead and the elongation component is inflated to stretch the spring mechanism, the distal portion is forced forward to advance along the lead because the proximal anchoring component provides greater resistance against movement relative to the lead despite the constant friction of the distal anchoring component. When the elongation component and the proximal anchoring component are deflated, the constant friction component provides greater resistance against movement such that as the spring mechanism returns to repose, the proximal portion (disengaged) is pulled towards the distal portion to advance the device along the lead.

A purpose of some embodiments of a lead extraction device is to separate tissue that has grown on or attached itself to the lead to facilitate lead removal without unnecessarily tearing and/or damaging the surrounding tissue. As discussed above, separation may be performed by providing a cutting portion (e.g., a knife or blade) having one or more edges designed to cut tissue to help in separating tissue from the lead. In some embodiments, the forward motion of the lead extraction device provides the force to separate tissue from the lead. However, in other embodiments, the cutting capabilities of the lead extraction device may be improved by adding rotation in addition to forward motion. A number of non-limiting embodiments of rotating cutting portions are described in further detail below.

Figure 6A:
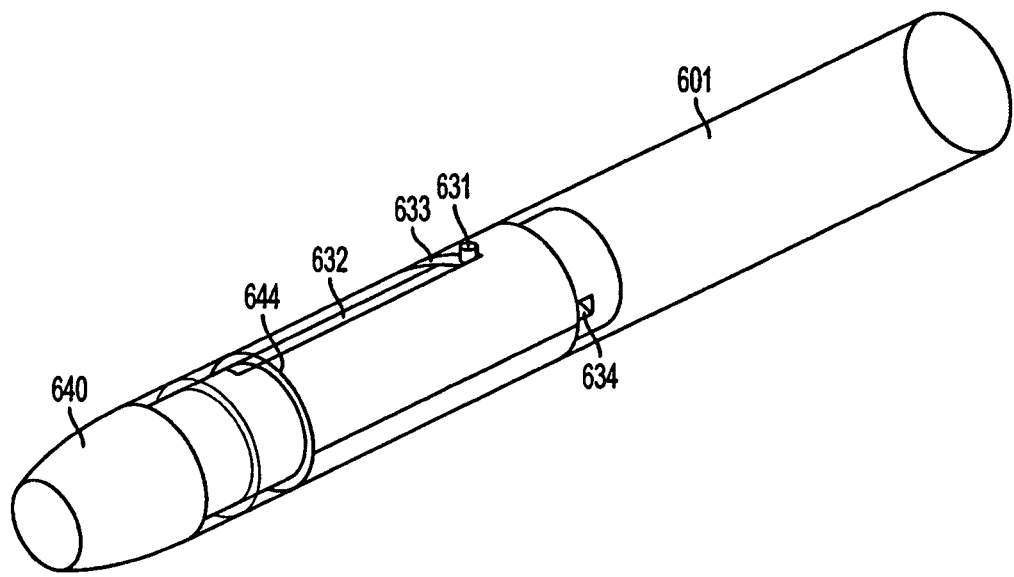
FIGS. 6A and 6B illustrate a portion of a lead extraction device comprising a slot and pin mechanism that allows for rotations of the cutting portion during operation, in accordance with some embodiments of the present invention.
Figure 6B:
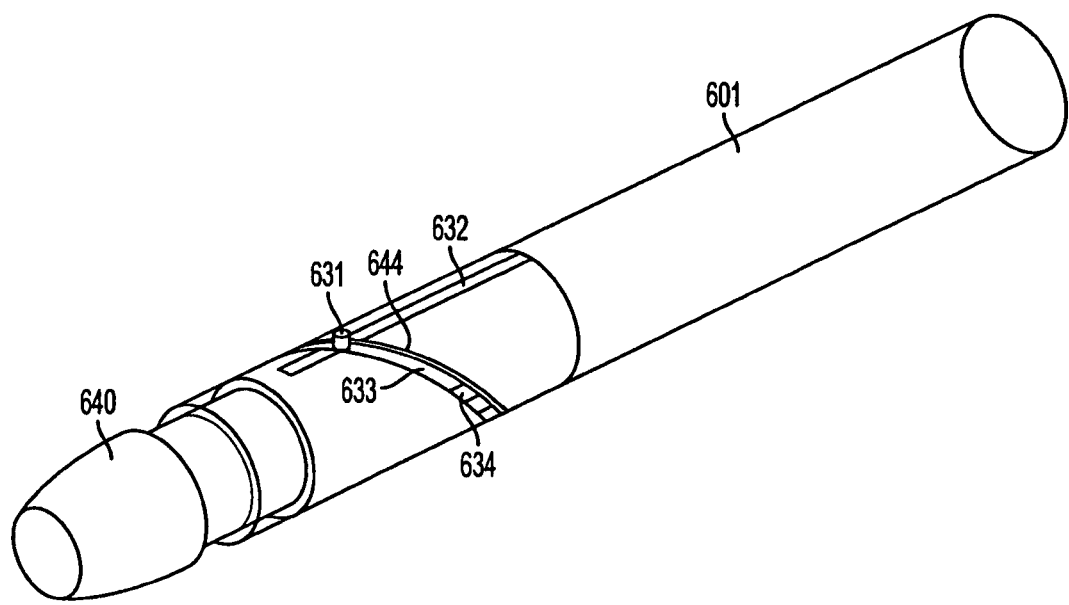

FIGS. 6A and 6B illustrate a slot and pin mechanism that allows for rotations of the cutting portion during operation. FIG. 6A illustrates a lead extraction device have a cutting portion coupled to a rotation mechanism that causes the cutting portion to rotate during advancement of the distal end of the device, in accordance with some embodiments. In FIGS. 6A and 6B, components involved in rotation are illustrated while other components of the device may be omitted in the drawing, though discussed in the description. The portion of the device includes a relatively rigid tube 601, a cutting portion 640, and a rotation component including a member 634, member 644, pin 631, axial slot 632, and diagonal slot 633.

Member 634 is coupled to the distal portion of the device and is forced forward when the device is elongated (e.g., upon inflation of one or more elongation balloons) and pin 631 is attached to member 634. Member 644 is coupled to the cutting portion and includes diagonal slot 633. As member 634 is advanced forward, the pin presses against the diagonal slot causing member 644 to rotate and advance, thus causing the cutting portion to simultaneously rotate and advance to cut incident tissue during the elongation phase of the lead extraction device. The pin and slot mechanism may be implemented in other ways, as the aspects of the invention are not limited in this respect.

Figure 7A:
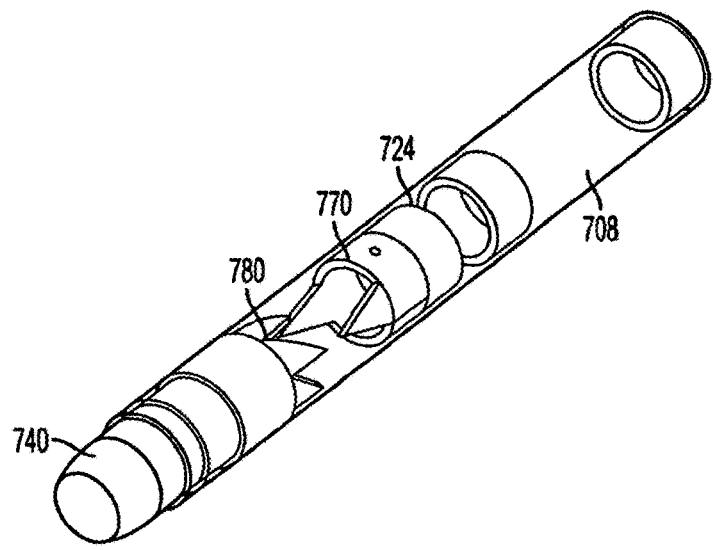
FIGS. 7A and 7B illustrate a portion of a lead extraction device having a cutting portion coupled to a rotation mechanism, in accordance with some embodiments of the present invention.
Figure 7B:
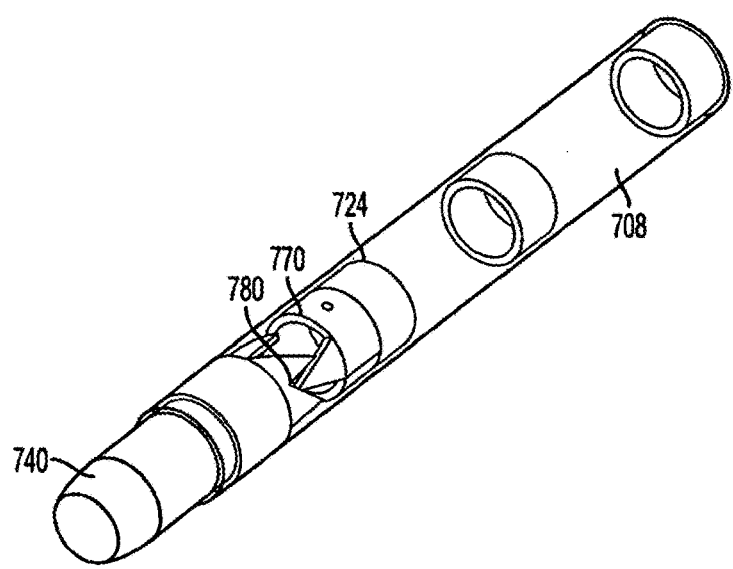

FIGS. 7A and 7B illustrate a lead extraction device having a cutting portion coupled to a rotation mechanism, in accordance with some embodiments of the present invention. The premise behind the operation of the rotation mechanism in FIG. 7 involves the interlocking of reciprocal components, for example, interlocking teeth, prongs or other cooperating structures that can be engaged. In FIG. 7, components involved in rotating the device are illustrated while other components may be omitted. The lead extraction device includes a relatively rigid tube 708, a portion of which may form the outer diameter of a proximal anchoring balloon.

A rotation component is comprised of two cooperating rotating members 770 and 780, each having reciprocal teeth that correspond to one another and engage when brought together. Member 724 moves with the distal portion of the device and is attached to one side of member 770. Accordingly, when member 724 is forced forward (e.g., by inflation of an elongation balloon), member 770 is also moved forward to engage with member 780 as illustrated in FIG. 7B. Member 780 is in turn coupled to the cutting portion 740. Once members 770 and 780 engage, the cutting portion will rotate as member 770 is force forward and rotates do the elongation operation of the device. When the elongation component contracts, the members 770 and 780 disengage and return to the position illustrated in FIG. 7A. Thus, the cutting portion is rotated during the elongation stage of the operation cycle only.

Figure 8:
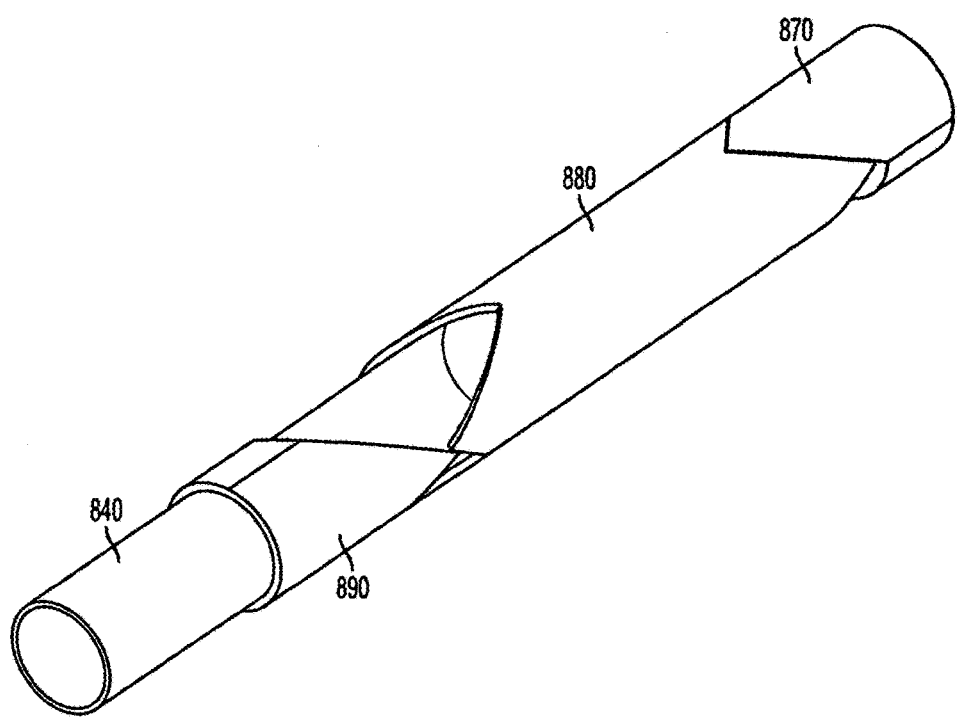
FIG. 8 illustrates the front portion of a lead extraction device having a cutting portion coupled to a rotation component, in accordance with some embodiments of the present invention.

FIG. 8 illustrates the front portion of a lead extraction device having a cutting portion coupled to a rotation component, in accordance with some embodiments of the present invention. As discussed above, components effecting a rotation of the cutting portion are illustrated while other components may be omitted. The lead extraction device in FIG. 8 is designed with a rotation component capable of rotating the cutting portion both during elongation (e.g., advancement of the distal portion) and during contraction (e.g., advancement of the proximal portion). The rotation component includes three rotation members 870, 880 and 890. Rotation members 870 and 880 may be similar in principle and operation to the coopering rotating members 770 and 780 described above in connection with FIGS. 7A and 7B, in that when rotating member 870 is forced forward and rotates, it rotates the cutting portion 840 when it engages with rotating member 880 to effect a forward advancement and rotation of the cutting portion during forward advancement of the distal portion (e.g., during an elongation phase).

In addition, rotating member 880 includes teeth structures to engage with both the rotating member 870 and rotating member 890, the latter of which effects rotation of the cutting portion during the advancement of the proximal portion of the device (e.g., during a contracting phase). Rotating member 890 may be slid over the cutting portion and forced to move in the same direction as rotating member 870. When the expansion portion of the device is elongated, rotating member 870, and thus rotating member 890, are forced towards the distal end of the device.

As discussed above, rotating member 870 engages rotating member 880 to advance and rotate the cutting portion as the expansion portion is elongated. When the expansion portion is contracted, the rotating member 870 moves back towards the proximal end, forcing rotating member 890 in the same direction. Since rotating member 880 remains static in the absence of forces from the other rotating members, rotating member 890 engages with and rotates rotating member 880 as it moves towards the proximal end. The rotation of rotating member 880 causes the cutting portion to rotate both in the elongation and contraction stages (e.g., both when the distal portion advances along the lead and when the proximal portion advances along the lead).

Figure 9:
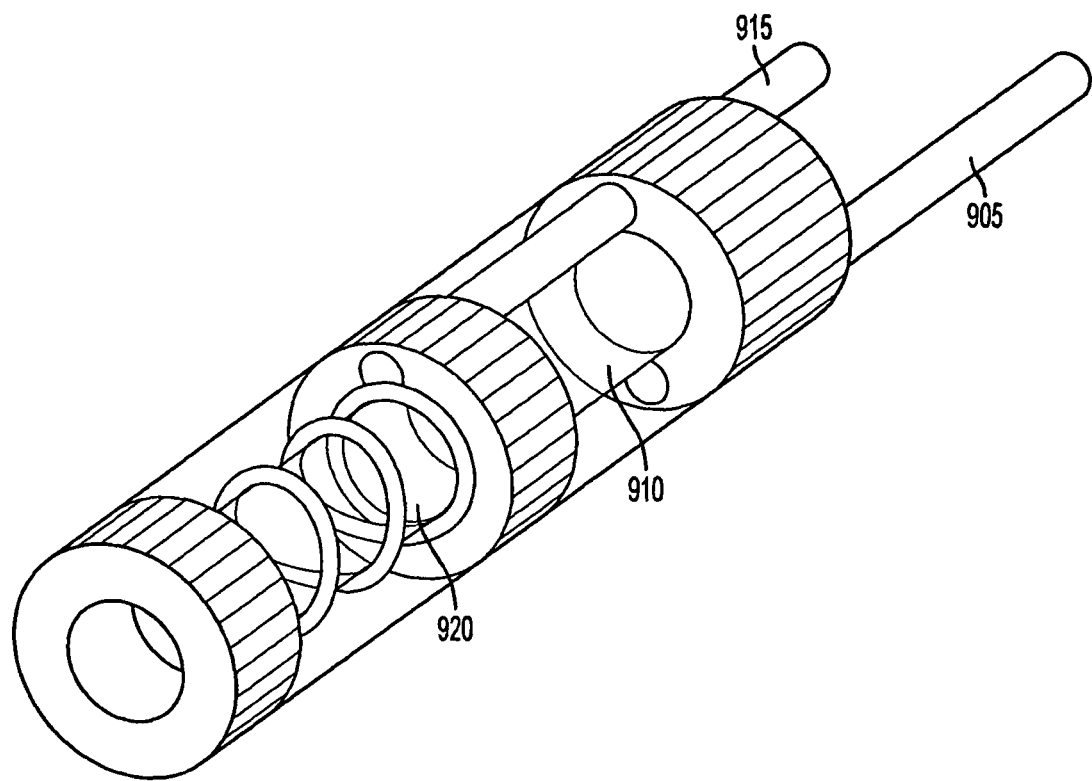
FIG. 9 illustrates a portion of a lead extraction device having inflation tubes to inflate the anchoring and expansion components, in accordance with some embodiments of the present invention.

Some aspects of the invention incorporate the underlying concept of utilizing fluid pressure changes to effect anchoring, advancing and/or cutting. According to some embodiments, fluid pressure changes cause balloons to either inflate or deflate. There are numerous ways in which the balloons can be inflated/deflated to affect anchoring, advancing and/or cutting by a lead extraction device. FIG. 9 illustrates inflating balloons via tubes, in accordance with some embodiments of the present invention. In FIG. 9, a tube 905 is coupled to proximal anchoring balloon 910 such that fluid may be forced into the proximal anchoring balloon to inflate the balloon to grip the lead. Similarly, tube 915 is coupled to elongation balloon 920 such that fluid may be forced into the balloon to elongate the balloon and stretch the spring mechanism.

In embodiments including a distal anchoring balloon, a third tube may be implemented to inflate the distal anchoring balloon in the same manner. The tubes may be of any type capable of providing fluid to the respective balloons (e.g., air, liquid or a solid such as foam). For example, the tube may have an accordion shape and/or be capable of being stretched. While the cross-section of the inflation tubes are shown as circular, the cross-section may be of any shape (e.g., elliptical), as the aspects of the invention are not limited in this respect. Alternatively, inflation may be achieved by annular tubes concentrically arranged about each of the respective components being inflated, as discussed in further detail below.

The inflation tubes may be coupled to a respective pump mechanism that allows fluid to be pumped into the device (e.g., into the respective balloon). For example, the pump mechanism may be a syringe with a spring and by pressing the syringe handle or plunger forces air/fluid into the balloons. In some embodiments, the fluid is a liquid (e.g., water, saline or some other desired solution), thus utilizing hydraulics to operate the lead extraction device. In some embodiments, the fluid is a gas (e.g., compressed air or some other gas such as an inactive or inert gas), thus utilizing pneumatics to operate the lead extraction device. In some embodiments, a combination of hydraulic and pneumatic techniques may be used to operate the lead extraction device, as the aspects of the invention are not limited in this respect.

According to some embodiments, the pump mechanism may be a squeeze pump that can be manually squeezed to fluid into the balloons (e.g., similar to squeeze balls commonly used to inflate blood pressure arm bands). The squeeze pump may include a release valve to release the pressure for deflation. Any of the various suitable pump mechanisms may be connected to a motor to inflate the respective balloons. For example, the pump mechanism may be part of a compressor unit capable of producing forced fluid. As an alternative to the embodiments discussed above in which fluid is delivered to the balloons via one or more inflation tubes, fluid may be delivered to the device via one or more annular tubes provided concentrically around the balloons. It should be appreciated that the balloons may be inflated/deflated by any other suitable means, as the aspects of the invention are not limited to any particular method by which balloons are inflated/deflated.

It should be appreciated that although in some embodiments one or more balloons may be inflated by forcing liquid into the balloons(s), aspects of the present invention are not limited in this respect. For example, in some embodiments, the balloon(s) may be inflated using gas. In such embodiments, a balloon being inflated by gas may be encased in an outer balloon to protect against puncture or accidental bursting. Such double balloon anchoring provides additional safeguards when inflating one or more balloons with gas rather than fluid. Any suitable gas may be used as the aspects of the present invention are not limited in this respect.

Figure 10:
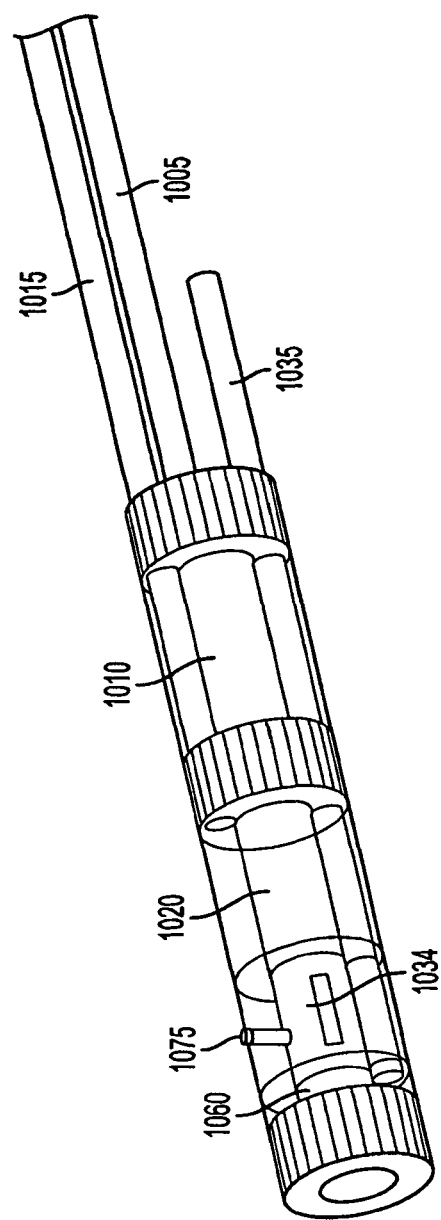
FIG. 10 illustrates a portion of a lead extraction device capable of operating without the use of a spring, in accordance with some embodiments of the present invention.

FIG. 10 illustrates a portion of a lead extraction device capable of operating without the use of a spring, in accordance with some embodiments of the present invention. The advancement of the lead extraction device in FIG. 10 may be powered by a mechanism capable of achieving sufficient forces when both inflating and deflating an elongation balloon. As with the lead extraction device described in connection with FIG. 9, balloons may be inflated and/or deflated via tubes. In particular, a proximal anchoring balloon 1010 is inflated and/or deflated via inflation tube 1005 and elongation balloon 1020 is inflated and/or deflated via inflation tube 1015. The proximal anchoring balloon and elongation balloon may operate in a manner similar to any of the mechanisms described herein. Elongation balloon 1020 pushes part 1034 of the distal portion forward and rotates (via the rotation mechanism 1075) the knife to advance the distal portion of the device forward.

Instead of having the tension in a stretched spring mechanism pull the proximal portion of the device towards the distal portion, a contracting balloon 1060 may be provided to perform substantially the same function. The energy stored in a stretched spring is replaced by energy stored in an inflated contracting balloon 1060. That is, after elongation and while elongation balloon 1020 is still inflated, the contracting balloon 1060 may be inflated to resist the distal portion and the proximal portion from coming together (e.g., similar to the resistance proffered by a stretched spring). The elongation balloon and the distal anchoring balloon may be deflated. The subsequent deflating of the contracting balloon releases the resistance and pulls the proximal portion towards the distal portion to complete the advancement of the device. This process may be repeated to advance the device along the lead. It should be appreciated that any of the cutting portions and/or rotation components discussed above can be incorporated into the springless embodiment described above in connection with FIG. 10, as the aspects of the invention are not limited for use with any particular combination of components.

As discussed above, some conventional lead extraction devices require the physician/surgeon to fully operate the device manually. This process may include manually securing one end of the lead (e.g., the portion protruding from the body and/or the portion that has been already extracted) while manually forcing the device forward to cut any connected tissue (e.g., by forcing forward a sheath having a knife on the distal end to engage with tissue interfering with the removal of the lead). This process can be very awkward for the surgeon and may be prone to error. To facilitate simpler lead extraction, various concepts described herein may be used alone or in different combinations to provide improvements to the fully manual lead extraction device. Several examples of lead extraction devices using anchoring concepts are described in further detail below.

Figure 11A:
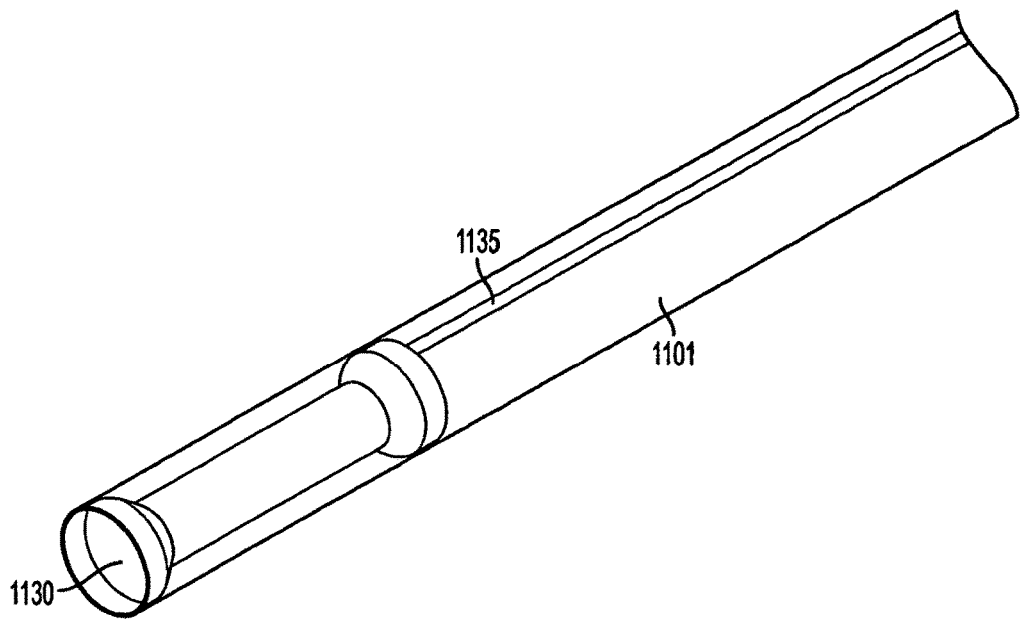
FIG. 11A illustrates a portion of a lead extraction device that uses internal anchoring to assist in lead extraction, in accordance with some embodiments of the invention.
Figure 11B:
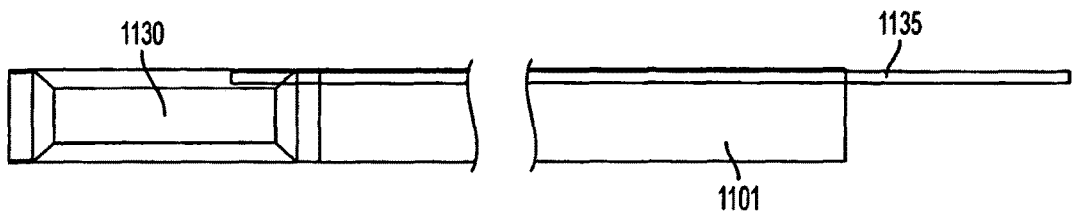
FIG. 11B illustrates a cross-section of the portion of the lead extraction device illustrated in FIG. 11A.

FIG. 11A illustrates a portion of a lead extraction device that uses internal anchoring to assist in lead extraction, in accordance with some embodiments of the invention. FIG. 11B illustrates a cross-section of the portion of the lead extraction device illustrated in FIG. 11A. According to some embodiments, an anchoring balloon 1130 is provided on a distal end of a lead extraction device. As discussed above, some conventional techniques for lead extraction involve threading a sheath having a distal cutting portion over the lead and manually forcing the sheath against obstructing tissue and/or twisting the sheath to facilitate cutting of the surrounding tissue. One or more anchoring balloons added to the distal end of such a device may facilitate separating the lead from the surrounding tissue.

In FIG. 11A, a portion of a device is illustrated having a sheath 1101. Sheath 1101 may be a conventional sheath or any type of sheath capable of being threaded over the lead. Preferably, the sheath has a relatively low rigidity for bending, but relatively high rigidity with respect to buckling and twisting. However, any suitable sheath may be used, as the aspects of the invention are not limited for use with any particular type of sheath or outer shell/body. The sheath may include a cutting portion on the distal end or may be provided without a cutting portion. One or more anchoring balloons may be provided at the distal end of the sheath. For example, an anchoring balloon 1130 of the type discussed herein may be provided such that the sheath can be anchored to and released from the lead as desired.

To operate the device, a surgeon may thread the sheath over the lead and push the device until it reaches attached tissue. The surgeon may then inflate anchoring balloon 1130 via inflation tube 1135 to anchor the device to the lead. With the device anchored proximate the attached tissue, the surgeon may pull on the device to release the lead from the attached tissue. The surgeon may also affect a twisting motion to assist in releasing the lead from the surrounding tissue. It should be appreciated that the surgeon may grip, pull and/or twist the device manually or may use other devices to assist and facilitate this motion, as the aspects of the invention are not limited in this respect. It should be appreciated that such a device may also be used in conjunction with an internal wire device that threads through the lumen of the lead and anchors to the internal lead wire coil, as discussed in the background section. For example, an anchored wire guide device may be pulled while the device is being pushed forward to the tissue and/or during the interval when the surgeon pulls/twists the anchored lead extraction device.

According to other embodiments, one or more proximal anchoring balloons may be used to facilitate extraction of a lead from a body. For example, the balloon illustrated in FIGS. 11A and 11B may be provided on the proximal side of the lead extraction device to assist in anchoring the device as a surgeon forces a connected distal portion forward along the lead. For example, the lead extraction device may have a distal portion that can be advanced independently of the proximal portion, such as a device that has an inner and an outer sheath, the outer sheath having a cutting portion that a surgeon can manually push forward to separate tissue from the lead. By providing one or more proximal anchoring balloons, the surgeon can position the device as desired and anchor the lead extraction device so that the surgeon does not have to both manually anchor the device and force forward the distal portion. Instead, the surgeon can focus on cutting the tissue at the distal end without having to worry about the proximal end of the device moving relative to the lead. This may result in freeing up one of the surgeons hand and decreasing the difficulty of the procedure.

Accordingly, some embodiments may include using only one or more proximal anchoring balloons. This anchoring balloon may be operated using manual pumps, automated pumps or other suitable mechanisms for inflating and deflating the one or more anchoring balloons. Such a tool may be advanced along the lead using manual forces, such as pushing on a sheath connected to the tool (e.g., the sheath described above), or using the tube attached to the anchoring balloon to push the tool forward. When the tool encounters an obstruction such as tissue, the proximal balloon may be inflated to anchor the tool and a cutting portion of the tool may be operated either manually (e.g., by a surgeon) or by using one or more automated mechanisms to operate the cutting portion to separate or cut the tissue. The tool may then be further manually advanced by pushing on the sheath, tubes, tool or other mechanically attached components. In other embodiments, additional balloons and/or pistons may be included in the device that can either be operated manually or automatically.

Various concepts related to anchoring, elongating and/or cutting may be improved using supplemental technology.

Figure 12A:
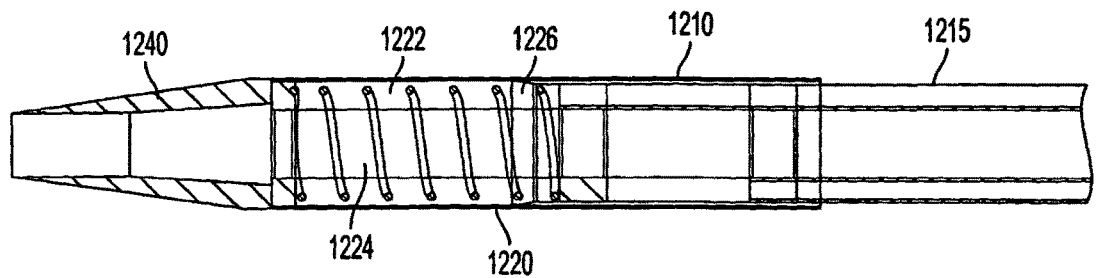
FIGS. 12A and 12B illustrate a lead extraction device having an extension portion formed from a relatively rigid outer tube and a flexible internal elongation tube, in accordance with some embodiments of the present invention.
Figure 12B:
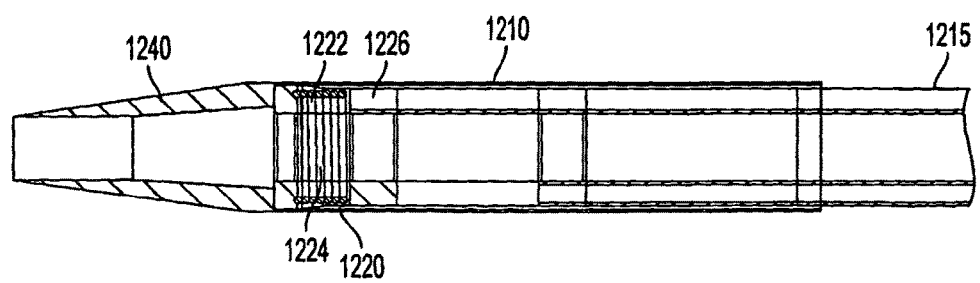

FIGS. 12A and 12B illustrate a lead extraction device having an extension portion formed from a relatively rigid outer tube and a flexible internal elongation tube. The relatively rigid outer tube may allow increased pressure upon inflation, thus increasing the force with which the cutting portion can be advanced/rotated along the lead, thereby improving the cutting ability of the device. For example, the lead extraction device illustrated in FIGS. 12A and 12B may include a cutting portion 1240, an expansion portion 1220, and a proximal portion 1210. The proximal portion 1210 may include one or more anchoring components of any type or combination of types described herein. Similarly, cutting portion may include any type of knife and may be provided with or without one or more rotating components described herein.

The expansion portion may be improved by providing both an outer tube 1222 that is relatively rigid (e.g., a steel or plastic tube) and an inner flexible elongation tube 1224. In addition, a seal 1226 may be provided between the cavity enclosing the expansion portion and the cavity enclosing the proximal anchoring component to prevent leakage from the elongation cavity to the anchoring cavity even under relatively high pressure. The seal may be of a conical shape and made of a relatively soft material such that when the inner elongation balloon is inflated, the fluid pushes the seal to against the outer tube, preventing leakage into the anchoring cavity (e.g., possible leakage in and around the inflation tube 1215). In addition, the seal may be arranged to prevent leakage external to the device. For example, when the expansion component elongates, the portion of component 1220 that slides over component 1210 is extended and a gap may form between the two components. The seal may be arranged to prevent fluid leakage outside the device via the gap under such circumstances.

The rigid outer tube prevents expansion of the elongation tube outward such that inflation pressure provides increased force in the longitudinal direction. The increased pressure that can be used to inflate the elongation balloon (e.g., due to the outer rigid tube and/or the seal) allows the expansion portion to advance/rotate the cutting portion with greater force, improving the cutting capabilities of the device. Other sealing mechanisms can be used to increase the pressure capacity of the device, as the aspects of the invention are not limited in this respect.

Figure 13:
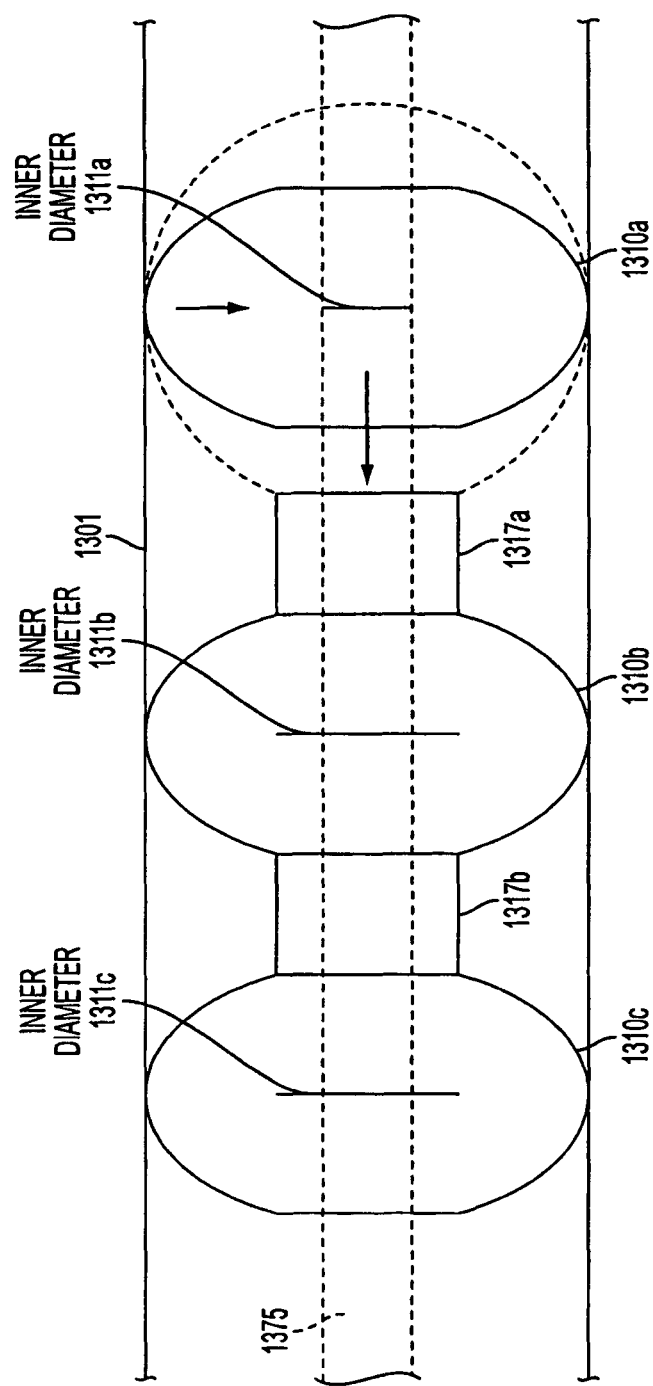
FIG. 13 is a schematic representation illustrating the principle of using a chain of balloons that each operate as both anchoring and elongation balloons, in accordance with some embodiments of the present invention.

Some aspects of the invention include using fluid pressure changes to anchor and advance/rotate a lead extraction device. For example, some embodiments include one or more anchoring balloons (e.g., proximal and/or distal anchoring balloons) and one or more elongation balloons. Applicant has appreciated that fluid pressure changes can be used to both anchor and advance/rotate a lead extraction using balloons that perform both anchoring and forward motion functions. FIG. 13 is a schematic representation illustrating the principle of using a chain of balloons that each operate as both anchoring and elongation balloons. FIG. 13 illustrates a portion of a lead extraction device having an outer tube 1301 formed from a relatively rigid material that substantially prevents balloons from inflating outwards.

The portion of the device also includes a chain of three balloons 1310*a*-1310*c*, with balloon 1310*a* on the proximal side of the chain and balloon 1310*c* on the distal side of the chain. The balloons may be toroidal in shape, spiral shape, or any shape having a center hole through which lead 1375 may be threaded. Balloons 1310 are connected via a connector 1317 that may include a relatively short length of pipe/tube and/or a valve that prevents fluid from flowing from one balloon to another until a desired pressure differential between the balloons is achieved. The balloons are illustrated in solid lines in the deflated state. The dotted line denotes the result of inflating balloon 1310a.

As shown, the inside diameters 1311 of the deflated balloons (e.g., balloons 1310b and 1310c) are wider than the diameter of the lead so that the balloons can move relative to the lead. When balloon 1310a is inflated (e.g., via an inflation tube), the balloon expands in the two directions indicated by the arrows. Specifically, the balloon expands such that the center hole constricts and grips the lead (as shown by the reduced inner diameter 1311a of balloon 1310a) and the balloon expands along the lead as indicated by the dotted lines. The outer tube prevents the balloon from expanding outwards. The expansion of balloon 1310a along the lead forces the adjacent balloon 1310b to advance along the lead. Fluid may be continually forced into balloon 1310a. When the pressure differential between balloon 1310a and balloon 1310b reaches a threshold value determined by the pipe and/or valve, fluid is forced into balloon 1310b and the balloon begins to inflate.

In a manner similar to balloon 1310a, balloon 1310b begins to inflate to both anchor the balloon to the lead and force adjacent balloon 1310c to advance along the lead. Because balloon 1310a is anchored to the lead, the expansion of balloon 1310b does not effect the location of balloon 1310a with respect to the lead. When the pressure differential between balloons 1310b and 1310c reaches a threshold, balloon 1310c begins to inflate. When all three balloons are inflated, each balloon is anchored to the lead and the distal end of the chain has been advanced along the lead (e.g., by the sum of the incremental advancements of each balloon in the chain). It should be appreciated that the last balloon on the distal end of the chain can be coupled to a cutting portion and/or rotation component such that the expansion of the chain forces the cutting portion forward and/or rotates the cutting portion to separate incident tissue.

To advance the proximal end of the chain, the balloons are iteratively deflated from the proximal end to the distal end in a similar manner. In particular, balloon 1310a may first be deflated, releasing the lead as the inner diameter returns to its deflated dimensions. Because balloon 1310b is still anchored to the lead, the connection between balloons 1310a and 1310b causes balloon 1310a to be drawn towards balloon 1310b to advance the balloon along the lead. When the pressure differential between balloons 1310b and 1310a reaches a threshold value, balloon 1310b begins to deflate, releasing the balloons hold on the lead. Because balloon 1310c remains anchored, balloons 1310b and 1310a are drawn towards balloon 1310c due to the connection and are advanced along the lead. When the pressure differential between balloons 1310c and 1310b reaches a threshold value, balloon 1310c begins to deflate, releasing the balloons hold on the lead. Subsequently, all balloons are deflated and return to the initial state but the chain has been advanced along the lead and the cutting portion has been forced forward and/or rotated. It should be appreciated that FIG. 13 is schematic to illustrate the principle and relative dimensions may not be accurate as certain components are enlarged to better illustrate the underlying concepts.

Any number of balloons may be used to form the chain adapted to both anchor and advance a lead extraction device along the lead, as the aspects of the invention are not limited for use with any particular number of balloons. Additionally, the linking component between the balloons may be any type of component that connects the balloons and allows fluid under pressure to pass between the balloons (e.g., that prevents fluid exchange until a desired pressure differential between adjacent balloons is reached and/or exceeded). The balloons in the chain can be formed from round torus shapes, cylindrical shapes or any other suitable shape that performs anchoring and advancement during an inflation/deflation cycle, as the aspects of the invention are not limited for use with balloons of any particular shape.

As discussed above, typical heart leads cover the inner wire (or wire coil) with a dielectric material. This material is often made from silicone or a polyurethane material. Materials used for constructing balloons may also be made from the same or similar materials. Accordingly, a problem may arise that when a balloon is in the deflated state, while not gripping the lead, the inner circumference may rest against and/or contact the lead. As a result, some amount of friction remains between the inner circumference of the balloon and the lead. Depending on the extent of this friction, proper advancement of the balloons may be partially or entirely impeded, frustrating advancement of the device. Rings inserted within the inner circumference of the balloon that have some spring resistance outward to force the inner circumference of the balloon away from the lead may be provided to prevent the inner circumferences of the balloon from providing drag on the lead when deflated, as discussed in further detail below.

Figure 14A:
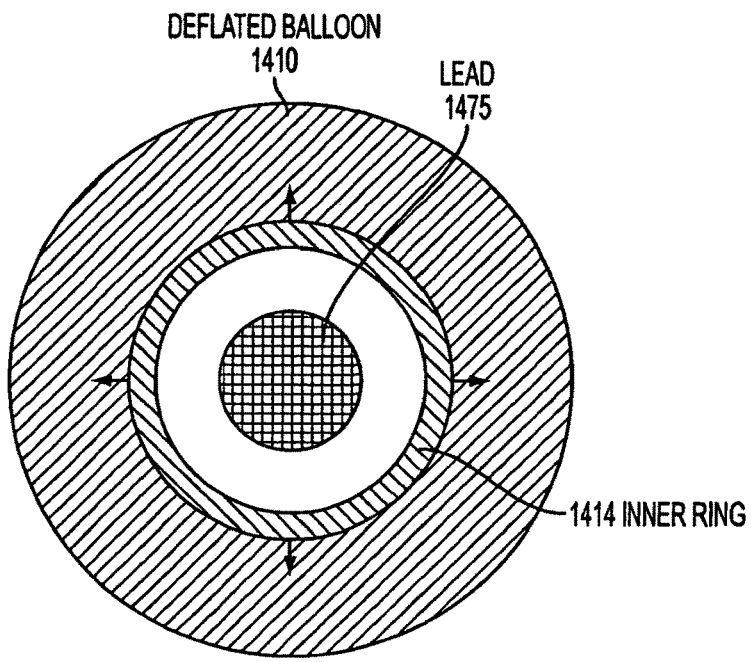
FIGS. 14A and 14B illustrate a cross-section of a balloon having a ring 1414 affixed to the inner circumference of balloon 1410, in accordance with some embodiments of the present invention.
Figure 14B:
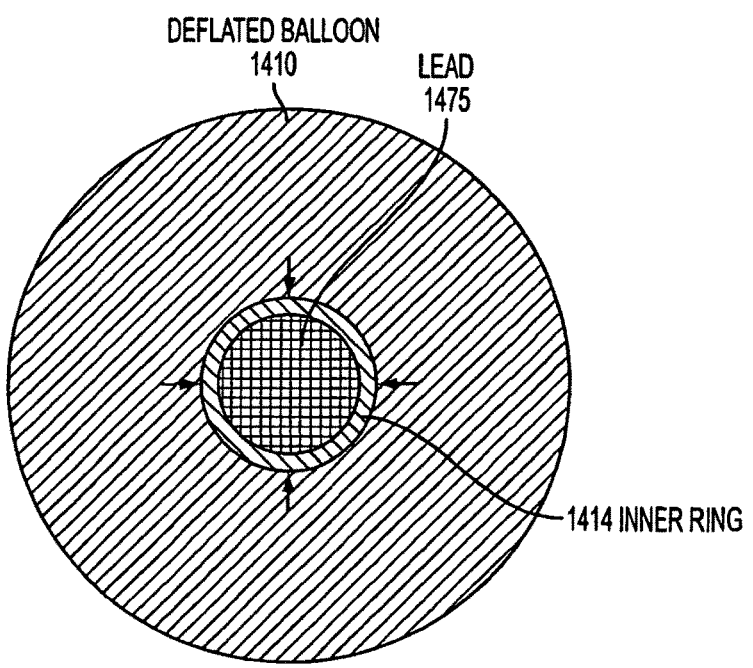

FIG. 14A and FIG. 14B illustrate a cross-section of a balloon having a ring 1414 affixed to the inner circumference of balloon 1410. Ring 1414 may be formed from an elastic material that in the absence of other greater forces, returns to a resting state wherein the diameter of the ring is as shown in FIG. 14A. However, the ring may be collapsible when an outside force is applied that is greater than the ring's natural tendency to conform to the shape illustrated in FIG. 14A. Thus, in the deflated state, the natural tendency of the ring to return to its maximum diameter forces the balloon 1410 away from the lead such that the balloon has little or no contact with the lead, allowing the balloon to move relative to the lead with relative freedom.

When the balloon is inflated, the force of the constricting inner circumference of the balloon becomes greater than the tendency of the ring to return to its maximum diameter. Thus, as the balloon inflates, the diameter of the ring collapses and grips the lead to anchor the balloon to the lead as illustrated in FIG. 14B. Application of the ring, therefore, may improve the operation of the balloon in the deflated state. It should be appreciated that ring 1414 may be formed from any suitable material that tends to a maximum diameter but whose diameter can be collapsed upon application of the force of an inflating balloon, as the aspects of the invention are not limited for use with rings of any particular material. Alternatively, stents may be used in place of the rings. For example, a mesh stent may be disposed proximate the inner wall of the balloon such that when the balloon is deflated, the stent forces the balloon away from the lead. Other methods of forcing the balloon away from the lead when deflated may also be used, as the aspects of the invention are not limited in this respect. The principle of providing a balloon that provides both anchoring and advancing functions can be implemented in any number of ways. FIGS. 15A-1, 15A-2, 15B, and 15C illustrate different views of a chain of balloons capable of both anchoring and advancing a lead extraction device. The chain of balloons may operate using the same or similar principle to that described in connection with FIG. 13. In the embodiments shown herein, balloons 1510 are cylindrical in shape, each connected to the adjacent balloon by a connector 1517, and inflated using inflation tube 1505. As shown in the cross-section view FIG. 15A-2 and the magnified view in 15B, the connectors 1517 may include a valve that allows fluid to flow to adjacent balloons once a pressure differential between the adjacent balloons has been achieved. It should be appreciated that the dimensions and specific implementation illustrated in FIGS. 15A-1, 15A-2, 15B and 15C is merely exemplary, and other dimensions, implementations, and components may be used, as the aspects of the invention are not limited in this respect.

According to some embodiments, the principle of using the same balloons for anchoring and advancing a lead extraction device is incorporated into a single balloon. For example, a single cylindrical balloon may be used wherein the connectors are rings that are slid over the balloon and pinched to a desired diameter to create a "neck" between the segments of the balloon. Referring to FIG. 15A-2, according to some embodiments, component 1500 may be formed from a single cylindrical balloon. Connectors 1517 may be rings inserted over the balloon that pinch the balloon into segments 1510a-1510c. The resulting neck therefore provides the "valve" mechanism that permits fluid flow between the balloons only when a desired pressure differential has been achieved between the balloons. Other implementations that use the principle of balloons or balloon segments that both anchor and advance a lead extraction device may be used, as the aspects of the invention are not limited in this respect.

FIGS. 16A, 16B, and 16C illustrate views of a lead extraction device incorporating at least some of the anchoring/advancing techniques discussed above in connections with FIGS. 13-15. In particular, component 1510 may be a chain of balloons or a chain of segments of a single balloon capable of both anchoring and advancing the lead extraction device. Any of the techniques described herein may be used to implement component 1510. In addition, component 1510 is coupled to a rotating component 1634 which is in turn coupled to cutting portion 1640. As component 1510 causes advancement, the rotation component 1634 is engaged and causes the cutting portion to rotate and advance to partially or completely separate tissue from the lead.

Rotation component 1634 may be the same or similar to any of the rotation components described herein or may be implemented in a different suitable manner, as the aspects of the invention are not limited in this respect. In addition, cutting portion 1640 may be any suitable component adapted to cut through tissue, in addition to a cutting portion adapted with heat, laser, and/or RF technology to soften/ablate tissue to facilitate cutting, as the aspects of the invention are not limited in this respect. The lead extraction device in FIG. 16 is illustrated as being inflated/deflated via inflation tube 1605; however, any inflation/deflation mechanism may be used.

Figure 17A:
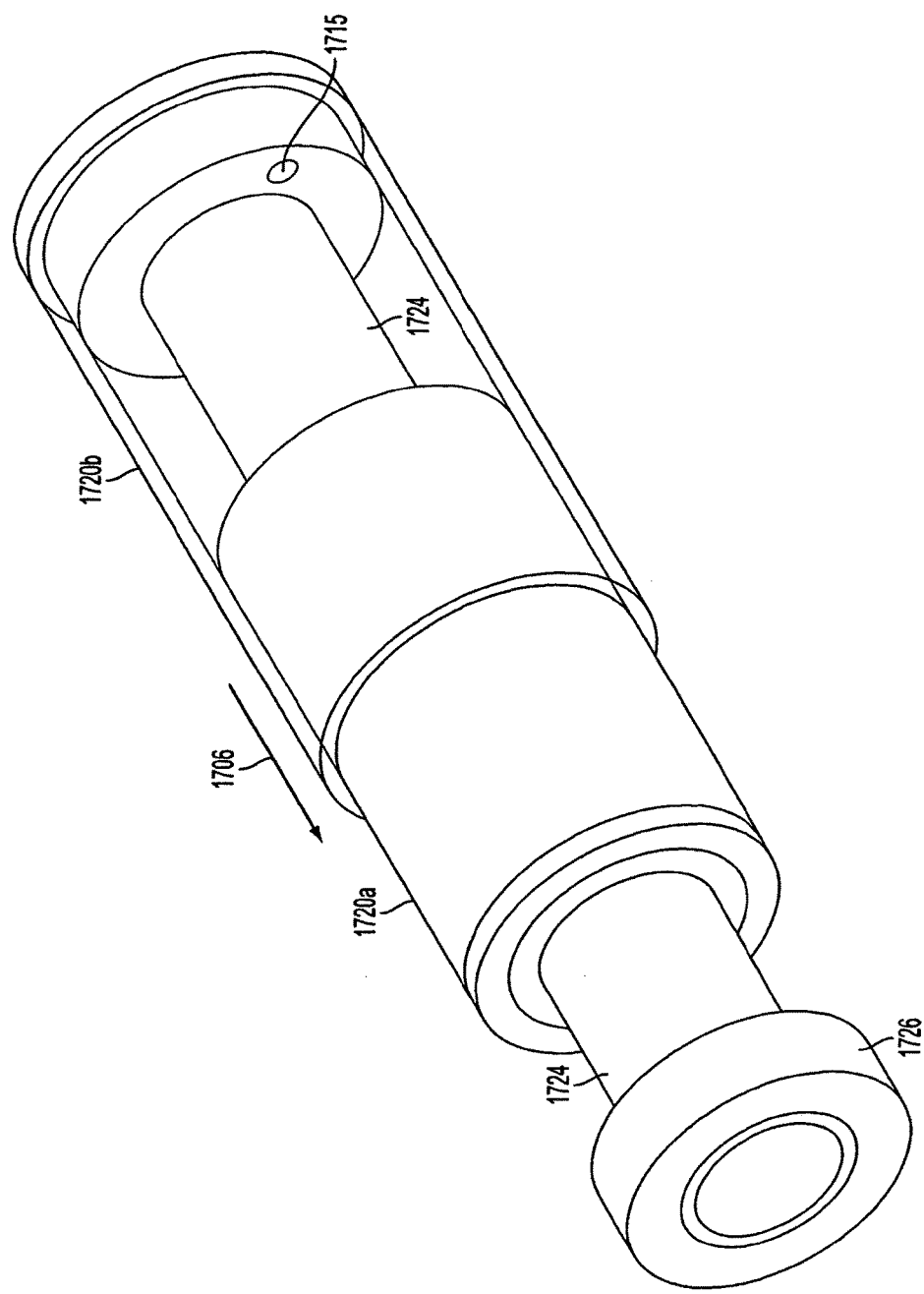
FIG. 17A illustrates a expansion portion for a lead extraction device using a piston mechanism, in accordance with some embodiments of the present invention.

FIG. 17A illustrates an expansion component for use with a lead extraction device, in accordance with some embodiments of the present invention. In FIG. 17, the expansion component uses a piston mechanism that may be either hydraulically or pneumatically operated to elongate a portion of the device to facilitate advancing the device along the lead. The expansion component may include a piston mechanism 1720, an inner tube 1724, and an end portion 1726. The piston mechanism 1720 may comprise inner part 1720a and outer part 1720b. The inner part 1720a may be moveably coupled to the outer part 1720b such that the inner part 1720a is capable of sliding into and out of outer part 1720b. Fluid pressure may be applied to the piston mechanism via hole 1715, which may in turn be connected to an inflation tube.

When fluid pressure is applied to the piston mechanism 1720, the inner part 1720a is forced out of outer part 1720b in the direction of arrow 1706. The inner part 1720a may be coupled to a cutting portion or a distal portion coupled to the cutting portion such that when the piston mechanism is inflated, the cutting portion is advanced forward. In addition, inner part 1720a may be coupled to a rotation component such that when the piston mechanism is inflated, the rotation component causes the cutting portion to rotate simultaneously with or independent from the forward motion of the cutting portion. The piston mechanism may be coupled to a spring mechanism such that when the piston mechanism is inflated, the spring mechanism is stretched. When the piston mechanism is deflated, the spring may recoil back to the repose position. The force of the spring mechanism returning to repose may force the inner part 1720a back into outer part 1720b (e.g., by pulling outer part 1720b forward).

Figure 17B:
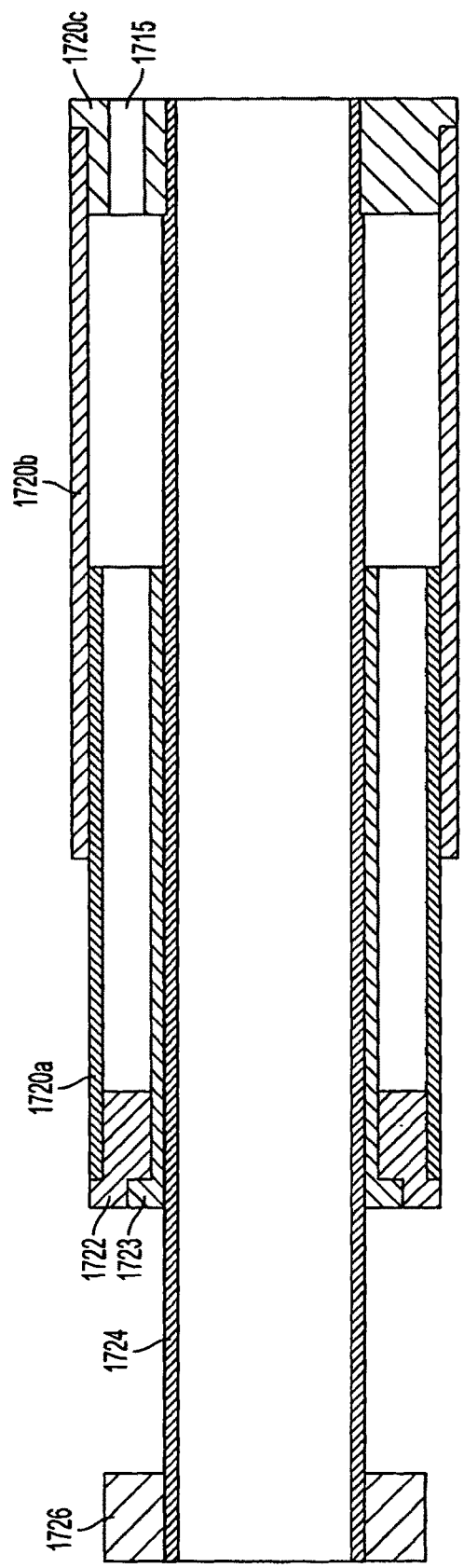
FIG. 17B illustrates a cross-sectional view of the expansion portion illustrated in FIG. 17A, in accordance with some embodiments of the present invention.

The inner tube 1724 may be a substantially rigid tube that accommodates the lead through the expansion portion. End portion 1726 may be arranged to stop the advancement of the inner part 1720a under fluid pressure. It should be appreciated that the expansion component may be used alone or with any one or combination of the other components described herein to facilitate advancement of a lead extraction device along the lead. Other piston mechanisms that elongate via fluid pressure may be used, as the aspects of the invention are not limited for use with any particular type of piston mechanism. FIG. 17B illustrates a cross-section of the expansion portion illustrated in FIG. 17A, showing parts 1722 and 1723 that allow the inner part 1720a to slide out under fluid pressure. In addition, part 1720c illustrates an end piece 1720c through which inflation tube can be inserted to inflate the piston mechanism.

Figures 1, 18A:
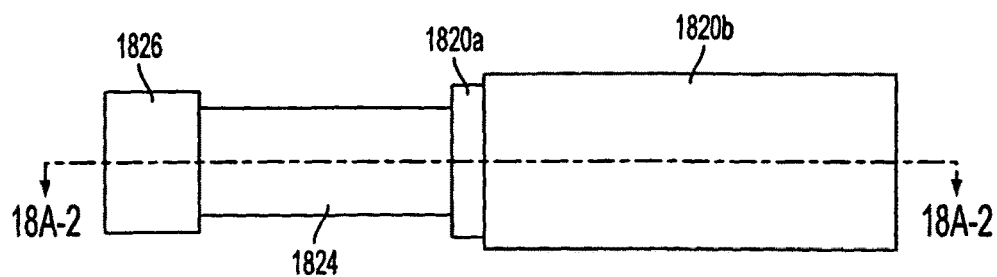
Figures 2, 18A:
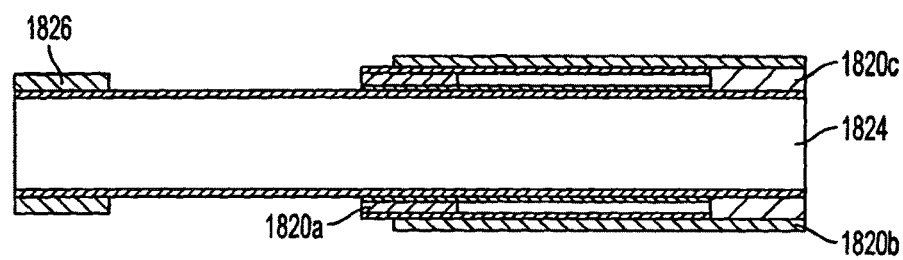
Figures 1, 18B:
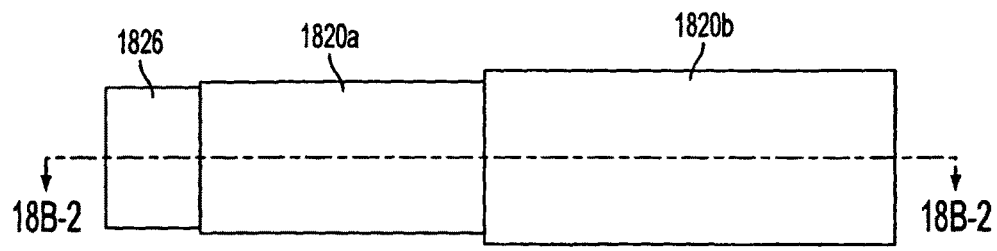
Figures 2, 18B:
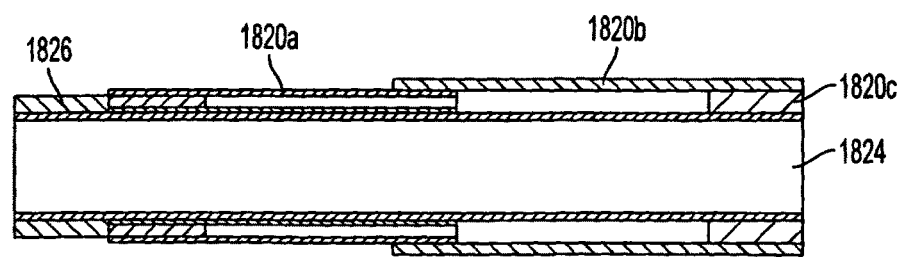

FIGS. 18A-1, 18A-2 and 18B-1, 18B-2 illustrate an expansion portion for a lead extraction device in a deflated state (both a normal view and a cross-section view) and in an inflated state (both a normal view and a cross-section view), respectively. The expansion portion includes a piston mechanism 1820 that may comprise an inner part 1820a, an outer part 1820b, and an end piece 1820c. The piston mechanism may operate in a manner similar or different from the piston mechanism described in connection with FIGS. 17A and 17B, as long as the inner part 1820a can be extended upon application of fluid pressure. As shown in FIG. 18A-1 and FIG. 18A-2, when the expansion component is in the deflated state, the inner part 1820a is substantially within outer part 1820b. When fluid pressure inflates the piston mechanism as shown in FIG. 18B-1 and FIG. 18B-2, inner part 1820a is forced outwards along the lead. Other parts, components, and mechanism may be included in the expansion portion, as the aspects of the invention are no limited in this respect.

In the above-described embodiments, a lead extraction device may comprise one or more components which may be hydraulically and/or pneumatically controlled. For example, a lead extraction device may comprise one or more balloons, one or more tubes, or any other suitable components that may be inflated or deflated by changes in fluid pressure. As another example, a lead extraction device may comprise one or more pistons that may expand/contract in response to changes in fluid pressure. Such pressure changes may be used to anchor and/or advance a lead extraction device over the lead and/or to cut/separate tissue from the lead.

Accordingly, in some embodiments, a control unit is used to control a lead extraction device by applying fluid pressure to the device. The control unit may be configured to iteratively generate changes in pressure in order to advance a lead extraction device over a portion of a lead and/or to cut/separate tissue from that portion of the lead. In some instances, the control unit may iteratively generate changes in pressure to advance the lead extraction device over a substantial portion of the lead (e.g. at least 75% of the length of the lead, at least 90% of the length of the lead, at least 95% of the length of the lead, at least 99% of the length of the lead, etc.) and/or to cut/separate tissue from that portion of the lead). In some instances, the control unit may apply fluid pressure according to a predetermined sequence to advance the lead extraction device as far as it needs to advance in order to release the lead so that it can be pulled from the body. According to some embodiments, the control unit independently operates the advancement of the tool and the cutting operation such that advancement may be performed alone, cutting may be performed alone, or both operations of advancement and cutting may be performed together.

The control unit may be operated in any of numerous ways. In some embodiments, the control unit may be handheld while operating to generate changes in pressure. In these embodiments, a human operator (e.g., a surgeon) may hold the control unit using one hand or using both hands, while the control unit operates to generate changes in fluid pressure. To facilitate the holding of the control unit by a human operator, in some embodiments, a handle may be attached to the control unit so that a human operator may hold the control unit by holding the handle. In other embodiments, the control unit may be a tabletop control unit adapted to be mounted or positioned on a surface (e.g., a table, a wall, a cart, etc.) while operating to control a lead extraction tool. In yet other embodiments, the control unit may be adapted to be handheld or be on a surface while operating to generate changes in pressure. In yet other embodiments, the control unit may be disposed on any other suitable structure adapted to hold the control unit and capable of being employed in a surgical environment. In some embodiments, the control unit is adapted to be of a size and weight such that the control unit is portable in nature, as discussed in further detail below.

The control unit may receive input from a human operator. The received input may provide an indication to start or stop advancement of the lead extraction tool over a portion of the lead and/or to start or stop tissue separation from that portion of the lead. For example, in some instances, input may be received as a result of a human operator providing manual input (e.g., pushing one or more buttons, operating one or more switches, turning one or more knobs, etc.). As a specific example, a human operator may push a button on the control unit to start operation of the control unit and may push another button to stop operation of the control unit.

Figure 19:
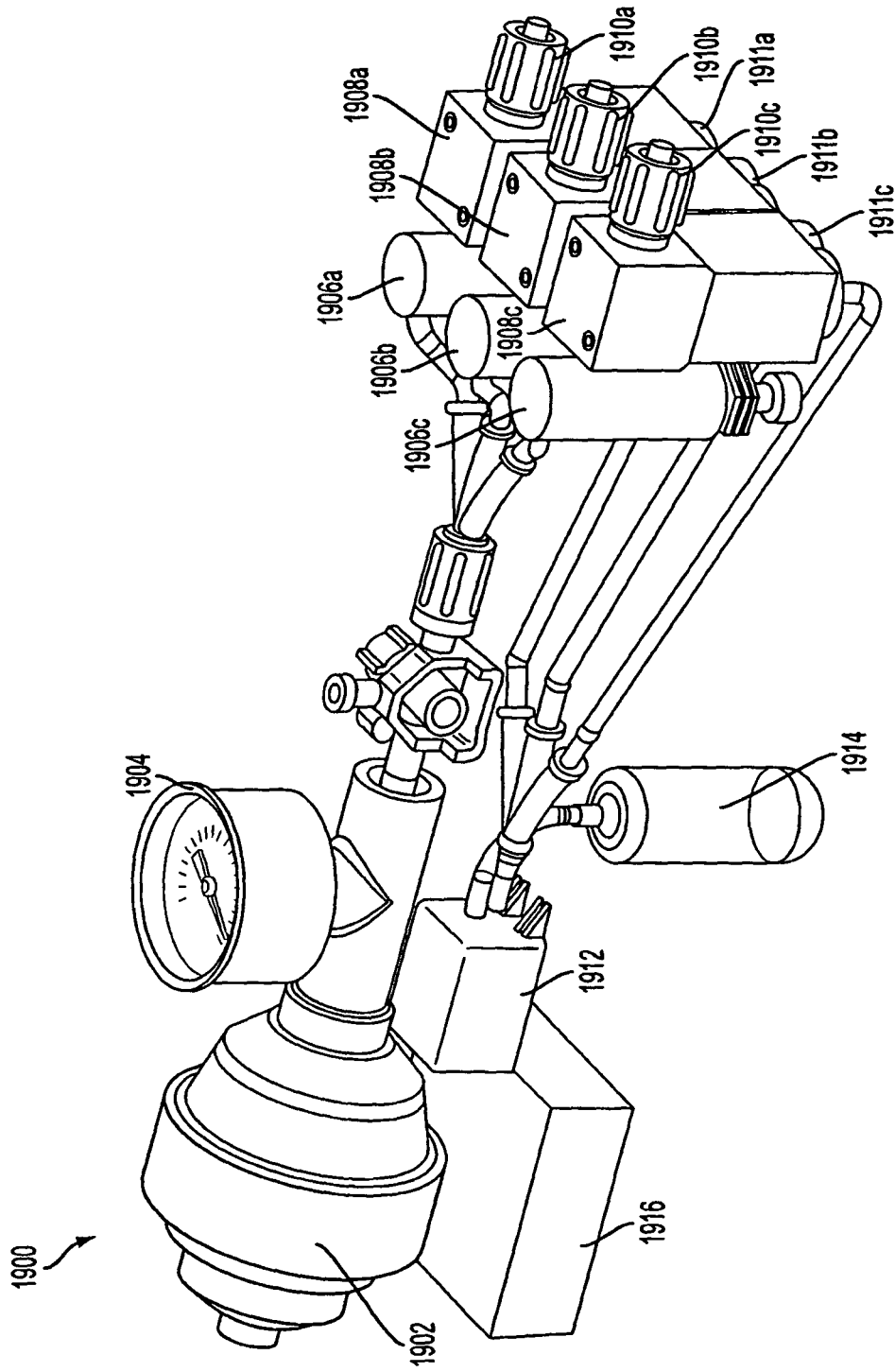
FIG. 19 illustrates a control unit for controlling a lead extraction device, in accordance with some embodiments of the present invention.

Any suitable type of control unit may be employed. In some embodiments, a control unit comprising at least one accumulator configured to store fluid under pressure may be employed. One such embodiment is illustrated in FIG. 19, which shows a control unit 1900 comprising an accumulator 1902 configured to store fluid under pressure and capable of releasing the fluid under pressure to control the operation of the lead extraction tool. In this capacity, the accumulator operates as a fluid reservoir to power the lead extraction via fluid pressure as it advances over the lead and/or separates tissue from the lead.

Accumulator 1902 may be configured to store any suitable and/or desired amount of fluid under any desired pressure conditions. Accumulator 1902 may be configured to store at least an amount of fluid needed to advance a lead extraction device over a substantial portion of the lead (e.g., at least 75% of the length lead, at least 90% of the length lead, at least 95% of the length of the lead, at least 99% of the length of the lead, etc.). In some embodiments, accumulator 1902 may be configured to store at least an amount of fluid needed to advance the lead extraction device as far as it needs to advance in order to release the lead so that it can be pulled from the body, or may store any additional amounts of fluid. In some embodiments, accumulator 1902 may be configured to store at least 100 cubic centimeters (ccs) of fluid under pressure, at least 200 ccs of fluid under pressure, at least 400 ccs of fluid under pressure, at least 600 ccs of fluid under pressure, etc.

Accumulator 1902 may be configured to store an amount of fluid under any suitable amount of pressure. Accumulator 1902 may be configured to store an amount of fluid under a an amount of pressure that is sufficient to advance a lead extraction device over the above-mentioned substantial portion of the lead by iteratively changing pressure in one or more components (e.g., one or more balloons, one or more tubes, one or more pistons, etc.) in the lead extraction device. In some embodiments, accumulator 1902 may be configured to store an amount of fluid under an amount of pressure that is sufficient to advance the lead extraction device as far as it needs to advance in order to release the lead so that it can be pulled from the body. In some embodiments, accumulator 1902 may be configured to store an amount of fluid at a pressure of at least 20 atmospheres (atms), at least 30 atms, at least 40 atms, at least 50 atms, at least 60 atms, at least 70 atms, at least 80 atms, at least 100 atms, etc.

Accumulator 1902 may be any of numerous types of accumulators configured to store an amount of fluid under pressure. In the illustrated embodiment, for example, accumulator 1902 may be a compressed gas accumulator. A compressed-gas accumulator may store a fluid under pressure by using a compressed gas to exert pressure on the fluid. A compressed gas accumulator may comprise a cylinder with two separated chambers. One of these chambers may be configured to hold compressed gas and the other chamber may be configured to hold fluid. The compressed gas held in one chamber of the accumulator may provide compressive force on the fluid held in the other chamber of the accumulator. The chambers may be separated in any of numerous ways and, for example, may be separated by a membrane. The gas may be inserted into the accumulator in any desired amounts to achieve a desired accumulator pressure for a given control application.

The accumulator may hold any suitable type of compressed gas, for example, an inert gas. In some embodiments, the gas may be nitrogen. Similarly, the accumulator may hold any suitable type of fluid. In some embodiments, the fluid may be a liquid (e.g., a sterile liquid such as water or saline) or a compressed gas (e.g., any inert gas).

Figure 20:
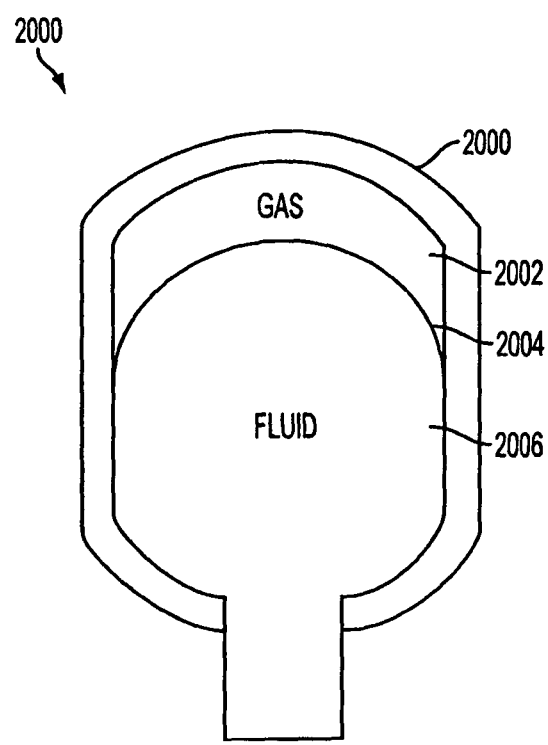
FIG. 20 illustrates a compressed-gas accumulator, in accordance with some embodiments of the present invention.

FIG. 20 shows a sketch of an illustrative compressed gas accumulator 2000. Accumulator 2000 comprises chambers 2002 and 2006 holding compressed gas and fluid under pressure, respectively. Chambers 2002 and 2006 are separated by membrane 2004. Though, it should be recognized that the accumulator illustrated in FIG. 20 is merely exemplary and any other type of compressed gas accumulator may be used.

Pressure in accumulator 1902 may be increased/decreased by increasing/decreasing the amount of fluid and/or gas in the accumulator. In some embodiments, a manual or an automatic pump/syringe may be used to fill accumulator 1902 with fluid thereby increasing the amount of fluid in accumulator 1902. Such a pump may be used to fill accumulator 1902 with any suitable amount of fluid including, but not limited to, any of the previously mentioned amounts of fluid that accumulator 1902 may hold. The fluid added to the accumulator exerts additional pressure on the membrane in turn exerting pressure on the gas in the accumulator and, as a result, increasing the pressure in accumulator 1902. Additionally or alternatively, the amount of gas in the accumulator may be increased/decreased to increase/decrease the pressure in accumulator 1902. Accumulator 1902 may be configured to release fluid. Releasing fluid from accumulator 1902 may decrease the pressure in accumulator 1902.

It should be recognized that accumulator 1902 is not limited to being a compressed gas accumulator and may be any suitable type of accumulator capable of holding a fluid under pressure. For example, in some embodiments, accumulator 1902 may be a spring-based accumulator comprising a chamber with fluid in it and at least one spring external to the chamber capable of providing compressive force on the fluid in the chamber. Pressure in a spring-based accumulator may be increased/decreased by increasing/decreasing the amount of fluid in the chamber and/or compressing the spring in the accumulator by application of an external force.

Figure 21:
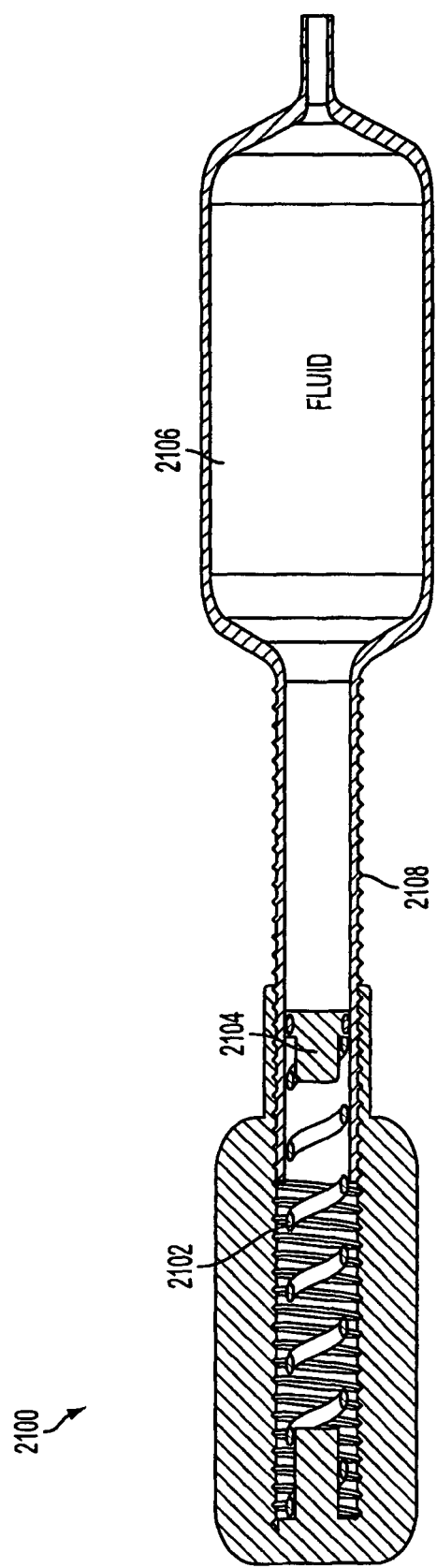
FIG. 21 illustrates a spring-based accumulator, in accordance with some embodiments of the present invention.

One example of such a spring-based accumulator is illustrated in FIG. 21, which shows illustrative spring-based accumulator 2100. Accumulator 2100 comprises spring 2102 coupled to membrane 2104. When spring 2102 is compressed, it provides a compressive force on fluid held in chamber 2106. Accumulator 2100 further comprises thread 2108 along which spring 2102 may be compressed by the application of an external force.

In the capacity described above regarding different embodiments of the accumulator, the accumulator operates as a hydraulic or pneumatic energy source, storing energy in the form of fluid pressure to power a lead extraction tool. In this sense, the accumulator operates as a hydraulic/pneumatic battery which can be "charged" beforehand by inserting a desired amount of fluid into the chamber and producing a desired pressure level (e.g., via gas compression, spring force, etc.) within the accumulator.

In addition to accumulator 1902, control unit 1900 may comprise various other components to transduce the potential energy stored in accumulator 1902 into forces that advance a lead extraction device along a lead and/or cause the lead extraction device to separate/cut tissue away from the lead. To this end, a control unit may comprise any of numerous other components including, but not limited to, one or more pressure regulators, valves, pumps, drain tanks, tubes, gauges, electrical components, micro-controllers, and/or any other suitable components, some of which are discussed in further detail below.

In the embodiment illustrated in FIG. 19, control unit 1900 further comprises gauge 1904 that may be used to measure and provide a reading of pressure in accumulator 1902. Pressure gauge 1904 may be any suitable type of gauge configured to measure pressure in accumulator 1902, as the aspects of the present invention are not limited in this respect. Use of a gauge is optional and is not necessary, but may provide useful pressure information both during "charging" of the accumulator and during operation to monitor the pressure in the accumulator during the course of a lead extraction procedure. In some cases, a gauge may be used to alert a human operator of control unit 1900 that pressure in accumulator 1902 has dropped below a certain level and/or that the volume of fluid in the accumulator is below a certain level.

Control unit 1900 may further comprise pressure regulators 1906a, 1906b, and 1906c and associated valves 1908a, 1908b, 1908c having openings 1910a, 1910b, and 1910c, respectively. In the illustrated embodiment, these components are fluidly coupled in a manner such that when valve 1908a is open, fluid from accumulator 1902 may flow through pressure regulator 1906a, through valve 1908a, and out through opening 1910a. Similarly, when valve 1908b is open, fluid from accumulator 1902 may flow through pressure regulator 1906b, through valve 1908b, and out through opening 1910b. Similarly, when valve 1908c is open, fluid from accumulator 1902 may flow through pressure regulator 1906c, through valve 1908c, and out through opening 1910c.

The term "fluidly coupled" refers herein to a coupling between components such that fluid from one component or portion of a component is capable of being transferred to another component or portion of another component to which it is fluidly coupled. The term fluidly coupled does not require direct fluid coupling nor does it impose any adjacency or proximity requirements, as components that are fluidly coupled may have one or more intervening components or may not have any intervening components, as the term is defined to cover both types of coupling.

Although not shown in FIG. 19, tubes may fluidly couple each of the openings 1910a, 1910b, and 1910c to one or more components of a lead extraction device. Such tubes may allow for fluid to flow from control unit 1900 to the lead extraction device and, subsequently, to fill and inflate one or more components (e.g., one or more balloons, tubes, pistons, etc.) in the lead extraction device. For example, fluid flowing out through any one of the openings 1910a, 1910b, 1910c, may flow through a tube and fill any of the balloons and/or tubes mentioned described herein (e.g., a proximal anchoring balloon, a distal anchoring balloon, an elongation balloon, a piston, etc.).

It should be appreciated that although controller 1900 comprises three pressure regulators and three valves, this is merely illustrative as control unit 1900 may comprise any suitable number of pressure regulators and/or valves to control the components of the lead extraction tool. For example, a lead extraction tool with a single component controlled by fluid pressure may need only a single regulator/valve combination, while lead extraction tools having multiple controlled components may need multiple regulator/valve combinations to suitably control the device. As such, controller 1900 may comprise any suitable number of pressure regulators and/or valves, coupled in any suitable way, so long as they are configured to allow for fluid to flow from accumulator 1902 to a lead extraction device to fill one or more components in the lead extraction device controlled via fluid pressure.

It should be appreciated that the pressure in accumulator 1902 may be greater than the pressure needed to inflate one or more components in a lead extraction device. As such, inflating a component of a lead extraction device by using fluid at a pressure of accumulator 1902 may exceed the amount of pressure that the component may be able to withstand, thereby damaging the component and potentially the lead extraction device. As a specific example, in some embodiments, pressure in accumulator 1902 may be at least 50 atmospheres, whereas a balloon in a lead extraction device may be inflated by applying a fluid having a pressure of 10-15 atmospheres. Accordingly, one or components of a control unit may be used to reduce the pressure of the fluid flowing from accumulator 1902 to one or more components of a lead extraction device.

In the illustrated embodiment, the above-mentioned pressure regulators 1906a, 1906b, 1906c, may be configured to perform this function of reducing the pressure of the fluid flowing from accumulator 1902 to one or more components in a lead extraction device. Any of numerous types of pressure regulators may be used, and may comprise one or more mechanical and/or electrical controls allowing the pressure regulator to be configured to reduce pressure of a fluid flowing through the pressure regulator by a predetermined amount and/or to a predetermined amount. In some embodiments, regulators may be unnecessary and the fluid pressure from the accumulator may be channeled to the lead extraction tool using other suitable means and methods.

The above-mentioned valves 1908a, 1908b, and 1908c may be any suitable types of valves. In some embodiments, valves 1908a-c may be controlled by application of an electric current. For instance, valves 1908a-c may be solenoid valves that may be controlled by the application of an electric current through one or more solenoids in the valves, and may be normally-closed or normally-open values, or some combination of each when multiple valves are present. Though, it should be appreciated that valves 1908a, 1908b, and 1908c are not limited to being solenoid valves and may be any of numerous other types of valves, controlled by any means including electrical, magnetic, mechanical (e.g., via a stepper motor) or by any other suitable means, as the aspects of the present invention are not limited in this respect. As such, a valve may be any device configured to regulate, direct, and/or control flow of a fluid. The valve may perform one or more of these functions by opening, closing, and/or partially obstructing one or more passageways. It should also be appreciated that, unless expressly indicated otherwise, a valve may refer to a device performing any of these functions, any components of the device (e.g., openings or ports), any components used to install the device (e.g., gaskets), as well as a portion of the passageway through which the device is configured to control the flow of fluid so that it may be said that fluid may flow through a valve when the valve is open.

In the embodiment illustrated in FIG. 19, each of valves 1908a-c comprises three openings: an opening for fluid flowing from a pressure regulator to enter the valve (not shown), an opening for fluid flowing between the valve and a lead extraction device (i.e., openings 1910a, 1910b, 1910c), and a drain opening for fluid flowing between the valve and drain tank 1914 (i.e., drain openings 1911a, 1911b, and 1911c) to allow fluid to be drained from the device, as discussed in further detail below.

As discussed above, when any one of valves 1908a-c is open, fluid may flow from accumulator 1902 through the open valve to a component in a lead extraction device. For instance, fluid may flow to a balloon in the lead extraction device and inflate it. On the other hand, when that valve is closed, fluid may flow away from a component in a lead extraction device, through the valve, and out the drain opening of the valve toward vacuum pump 1912. For instance, fluid may flow away from an inflated balloon in the lead extraction device toward drain tank 1914. When fluid flows away from a component in a lead extraction tool, the component may deflate (e.g., when fluid flows away from a balloon or a tube, the balloon, or the tube may deflate).

In some embodiments, vacuum pump 1912 may operate by drawing fluid away from a lead extraction device. In particular, when one of valves 1908a-c is closed, vacuum pump 1912 may operate to draw fluid away from the lead extraction device through the drain opening of the closed valve. As a specific non-limiting example, when valve 1908a is closed, vacuum pump 1912 may operate to draw fluid away from the lead extraction device, along a tube connecting a component of the lead extraction device to opening 1910a, through drain opening 1911a and toward vacuum pump 1912.

Vacuum pump 1912 may be any of numerous types of pumps. In some embodiments, vacuum pump 1912 may be a positive displacement pump. As a specific example, vacuum pump 1912 may be a peristaltic pump or any other type of pump that may be used in surgical or medical applications.

Control unit 1900 may further comprise drain tank 1914. Drain tank 1914 may be any suitable type of tank and may hold fluid drained through valves 1908a-1908c. In some embodiments, vacuum pump 1912 may operate to draw fluid away from a lead extraction device so that the drawn away fluid flows into drain tank 1914. As such, fluid initially in accumulator 1902 may flow toward the lead extraction device and, subsequently, may be drawn away from the lead extraction device and flow into drain tank 1914. Accordingly, in some embodiments, drain tank 1914 may have capacity to hold at least the amount of fluid that accumulator 1902 is configured to hold.

Accordingly, it should be appreciated that control unit 1900 may operate to cause changes in fluid pressure by operating valves 1908a-c and vacuum pump 1912. These pressure changes, in turn, cause fluid to inflate/deflate one or more components in a lead extraction device coupled to the control unit. In this manner, control unit 1900 may operate to advance a lead extraction device over a lead and/or cause the lead extraction device to separate/cut tissue away from the lead.

Control unit 1900 further comprises controller 1916. Controller 1916 may be any suitable type of computing device and may comprise one or more integrated circuits, one or more processors or processor cores, memory, and/or input/output peripherals. In some embodiments, controller 1916 may be in control unit 1900. In these embodiments, controller 1916 may be implemented using one or more micro-controllers, one or more integrated circuits, one or more programmable logic controllers, etc. Alternatively, controller 1916 may be external to control unit 1900 and control unit 1900 may be communicatively coupled to controller 1916. In these embodiments, controller 1916 may be implemented using any of numerous types of computing devices including laptops, desktops, hand held computing devices, personal digital assistants, tablet devices, and/or any other computing device comprising one or more processors and configured to communicate with control unit 1916. It should be recognized that control unit 1900 is not limited to having only one controller and, in some instances, may comprise multiple controllers.

Controller 1916 may be programmed to control one or more components of control unit 1900. As such, controller 1916 may be programmed to issue one or more signals to control one or more components in control unit 1900. In some embodiments, controller 1916 may be configured to control the opening and closing of valves 1908a-c. For example, when valves 1908a-c are solenoid valves, controller 1916 may be configured to cause the application of current to the solenoid valves to control opening and closing of the valves. Controller 1916 may also be configured to control the operation of vacuum pump 1912. For example, when one of valves 1908a-c is closed, controller 1916 may be configure to control vacuum pump 1912 to draw fluid away from the lead extraction device to which control unit 1900 is coupled. Though, it should be recognized that controller 1916 is not limited to controlling only valves 1908*a-c* and pump 1912 and may be configured to control any other suitable component of control unit 1900. For example, controller 1916 may be configured to control accumulator 1902 to release fluid.

It should also be appreciated that controller 1916 may be configured to control valves 1908*a-c* and vacuum pump 1912 to achieve changes in fluid pressure used to advance the lead extraction device along a lead and/or cause the lead extraction device to separate/cut away tissue from the lead. In some embodiments, controller 1916 may be configured to control the valves to repeatedly close and open, and the vacuum pump, in a sequence so as to advance the lead extraction device along the lead.

As a specific example, consider an embodiment in which control unit 1900 is coupled to a lead extraction device comprising three balloons: a proximal anchoring balloon coupled via a tube to opening 1910*a* of valve 1908*a*, an elongation balloon coupled via a tube to opening 1910*b* of valve 1908*b*, and a distal anchoring balloon coupled via a tube to opening 1910*c* of valve 1910*c*. In this embodiment, controller 1916 may control valve 1908*a* to open, thereby causing fluid from control unit 1900 (e.g., fluid from accumulator 1902) to flow and, as a result, fill and inflate the proximal anchoring balloon. Inflation of the proximal anchoring balloon may anchor the proximal portion of the lead extraction device to the lead. Next, controller 1916 may control valve 1908*b* to open, thereby causing fluid stored in control unit 1900 to flow and, as a result, fill and inflate the elongation balloon. Inflation of the elongation balloon may cause the distal portion of the lead extraction device to advance along the lead and/or for the cutting portion of the lead extraction device to separate/cut away tissue from the lead. Next, controller 1916 may control valve 1908*c* to open, thereby causing fluid from control unit 1900 to flow and, as a result, fill and inflate the distal anchoring balloon. Inflation of the distal anchoring balloon may anchor the distal portion of the balloon to the lead.

Next, controller 1916 may control valves 1908*a* and 1908*b* to close (sequentially or simultaneously) the valves and may operate vacuum pump 1912 to draw fluid away from the proximal anchoring balloon and the elongation balloon. Drawing fluid away from the proximal anchoring and elongation balloons may deflate these balloons and allow a spring in the lead extraction device to repose thereby bringing the proximal portion of the device toward its distal portion. Next, controller 1916 may control valve 1908*c* to close and may operate vacuum pump 1912 to draw fluid away from distal anchoring balloon. Drawing fluid away from the distal anchoring balloon may deflate the distal anchoring balloon and cause the device to return to its initial configuration. That is, each of the balloons in the lead extraction device may be deflated and the device returns to its initial configuration but has been advanced along the lead and may also separate (or at least partially cutting/separating) tissue encountered by the cutting portion during the incremental advancement of the above-described operation cycle.

Controller 1916 may control the valves and vacuum pump of control unit 1900 to repeat steps of the above-described operation cycle in order to continue to advance the lead extraction device forward until the device has advanced as far as it needs to advance in order to release the lead so that it can be pulled from the body. Controller 1916 is not limited to controlling components of control unit 1900 in the above-described order and may control components of control unit 1900 in any suitable order. Further, controller 1916 need not control components of control unit 1900 sequentially, and may control various components to operate simultaneously or have their operation overlap in time, as the aspects of the invention are not limited for use with any particular control timing scheme.

In addition, controller 1916 may process data gathered by one or more components of control unit 1900. For example, controller 1916 may process measurements gathered by one or more pressure sensors (e.g., pressure gauge 1916). Controller 1916 may use the data to affect the way it controls one or more components in the control unit. Additionally or alternatively, controller 1916 may present the data to a human operator of the control unit via one or more user interfaces.

It should be appreciated that although control unit 1900 was described being configured to hydraulically control the lead extraction device by issuing one or more signals to control components of the control unit in order to produce changes in pressure of a fluid to inflate/deflate the component(s) of the device, control unit 1900 is not limited to hydraulically controlling the component(s). In some embodiments, for example, control unit 1900 may pneumatically control one or more components of the lead extraction device, in addition to or instead of hydraulically controlling one or more components of the device. For example, changes in fluid pressure may be used to expand/contract one or more pistons in the device.

It should also be appreciated that control unit 1900 may comprise any other suitable components that may be needed to operate a lead extraction tool. For example, in embodiments in which a lead extraction tool comprises one or more rotating components (e.g., a rotating metal tip, a rotating shaft, etc.), control unit 1900 may comprise one or more components (e.g., one or more motors, gears, rotating shafts, etc.) used to drive the rotation. As another example, in embodiments where a lead extraction tool comprises one or more energy-emitting components (e.g., a laser, an RF transmitter, an ultrasound transmitter, etc.), control unit may comprise one or more energy sources for the energy-emitting components.

Figure 22:
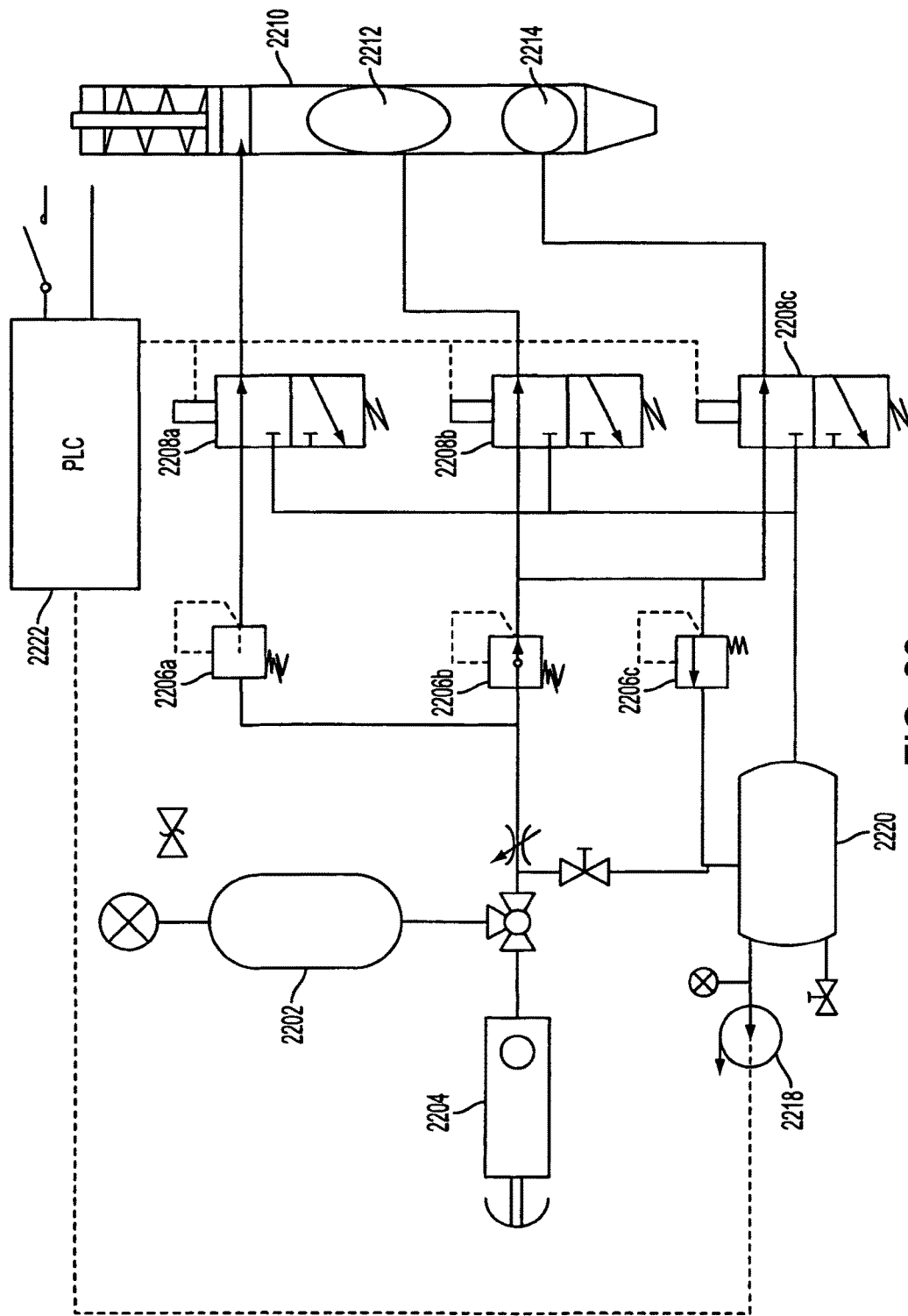
FIG. 22 illustrates a schematic representation of a control unit for controlling a lead extraction device, in accordance with some embodiments of the present invention.

FIG. 22 further illustrates how a control unit may be used to control a lead extraction device. In particular, FIG. 22 shows a schematic representation of a control unit and lead extraction device 2210. The control unit illustrated in FIG. 22 may be the same control unit as control unit 1900 or may be any other control unit.

The control unit illustrated in FIG. 22 comprises a compressed-gas accumulator 2202. Accumulator 2202 may be any suitable type of compressed-gas accumulator including, but not limited to, any of the compressed-gas accumulators previously described. Pressure in accumulator 2202 may be increased by introducing fluid into it, which, in the illustrated embodiment, may be performed by syringe/pump 2204. Syringe/pump 2204, which may be external to the control unit, may be used to increase pressure in accumulator 2202 to a desired level before the control unit is used to control lead extraction device 2210. As such, syringe/pump 2204 may be used to load accumulator 2202 with fluid that may be used to advance device 2210 along a lead and/or cause device 2210 to separate/cut away tissue from the lead. In some embodiments, syringe 2204 may be used to load accumulator 2202 with fluid while accumulator 2202 is inside the control unit. Alternatively, syringe 2204 may be used to load accumulator 2202 with fluid before accumulator 2202 is installed in the control unit.

In addition to accumulator 2202, the control unit illustrated in FIG. 22 may comprise any of various other components to transduce the potential energy stored in accumulator 2202 into forces used to advance a lead extraction device along a lead and/or cause the lead extraction device to separate/cut tissue away from the lead.

As such, the illustrated control unit comprises valves 2208*a*, 2208*b*, and 2208*c*, that, when open, are configured to allow fluid to flow from accumulator 2202, through pressure regulators 2206*a*, 2206*b*, and 2206*c*, through valves 2208*a*, 2208*b*, and 2208*c* toward lead extraction device 2210. The fluid may be used to inflate/deflate one or more components in device 2210 such as illustrated balloons 2212 and 2214. Though, it should be recognized that the fluid may be used to operate any other suitable component in device 2210 including one or more other balloons, one or more tubes, one or more pistons, etc. Any suitable pressure regulators and/or valves may be used including, but not limited to, the previously-described types of pressure regulators and valves. Similar to control unit 1900, it should be appreciated that the number of components in the control unit illustrated in FIG. 22 is merely illustrative. As such, a control unit may have any suitable number of pressure regulators (e.g., at least one, at least two, at least three, at least five, etc.) and any suitable number of valves (e.g., at least one, at least two, at least three, at least five, etc.). In some instances, the number of valves may be the same as the number of components in a lead extraction device that need to be controlled by the control unit. However, in other instances these numbers may be different.

The control unit further comprises vacuum pump 2218 that may operate to draw fluid away from device 2210, when one or more valves 2208*a*, 2208*b*, and 2208*c* is closed. In the illustrated embodiment, vacuum pump 2218 may be configured to draw fluid away from device 2210 and into drain tank 2220. Any suitable vacuum pump and/or drain tank may be used including, but not limited to, the previously described vacuum pump and/or drain tank.

The control unit further comprises programmable logic controller 2222 that may be configured to control or more components of the control unit. Controller 2222 is not limited to being a programmable logic controller and may be any suitable computing device including, but not limited to, any of the previously mentioned computing devices. In the illustrated embodiment, controller 2222 may be configured to control accumulator 22202, valves 2208*a-c*, and vacuum pump 2218. Though, it should be recognized that controller 2222 may be configured to control any other component of the control unit. Controller 2222 may control any of the above-mentioned components during operation of the control unit in order to affect changes in fluid pressure that, in turn, may be used to advance lead extraction device 2210 along a lead and/or cause device 2210 to separate/cut away tissue from the lead.

In some embodiments, a control unit may comprise one or more syringes instead of or in addition to an accumulator. Each syringe may be configured to hold a fluid under pressure. Each syringe may be controlled by at least one motor, at least one encoder (e.g., a rotary encoder), and a pressure gauge. Further, each syringe may be connected to a component in a lead extraction device (e.g., a balloon, a tube, a piston, etc.). Any of numerous types of syringes, motors, encoders, and pressure gauges may be used as the aspects of the present invention are not limited in this respect.

In some embodiments, a motor may rotate in one direction to increase pressure in a syringe to cause fluid to flow from the syringe toward a component (e.g., balloon, piston, etc.) in the lead extraction device, thereby inflating it. The motor may rotate in the other direction to decrease pressure in the syringe to cause fluid to flow away from the component in the lead extraction device back toward the syringe thereby deflating the component.

A control unit using one or more such syringes may further comprise a controller configured to control the motors to rotate in predetermined manner to affect the advancement of the lead extraction device along a lead and/or cause the device to separate/cut away tissue form the lead. The controller may be configured to control the motors to rotate so as to result in a series of inflation/deflation of lead extraction device components in a manner analogous to how those components inflate/deflate in the above-described embodiments. To this end, the controller may receive feedback from the one or more pressure gauges to determine when to start/stop rotation of the corresponding motors.

A control unit using one or more such syringes may further comprise any of numerous other components including pressure regulators and valves. For example, the control unit may use a single syringe and multiple valves to transfer fluid between the syringe and one or more components of the lead extraction device. Many other variations of the above-described control apparent to those of skill in the art are possible and are considered to be included in the scope of the present invention.

The inventors have appreciated that a lead may be curved when in the patient's body and the curves of the lead may have diameters of different sizes. In some instances, the curves may have small diameters. Thus, as a lead extraction device advances along the lead, the lead extraction device may need to advance along the lead in the region of a curve having a small diameter. Accordingly, introducing flexibility into a lead extraction device may aid the lead extraction device in advancing along the lead through small diameter curves. To this end, in some embodiments, a spring may be introduced between any two portions of the lead extraction device to make the device more flexible. Though, it should be recognized that aspects of the present invention are not limited to introducing a single spring between two portions of the lead extraction device and, in some embodiments, multiple springs may be used to make the device more flexible. In such embodiments, each of the multiple springs may be disposed between two portions of the lead extraction device.

Figure 23A:
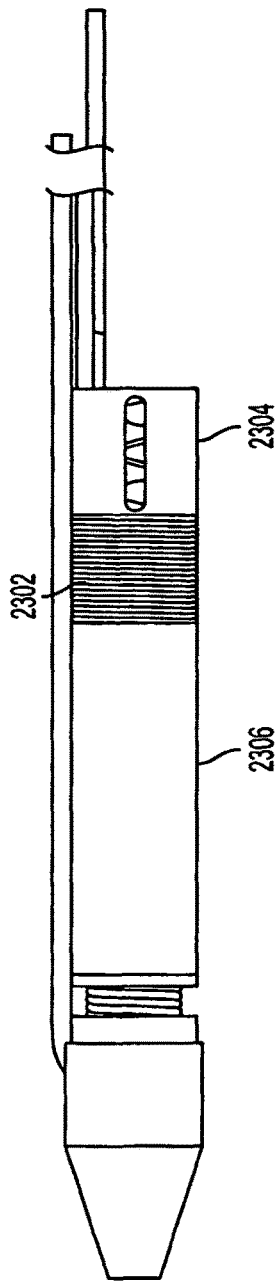
FIG. 23A illustrates a lead extraction device comprising a spring disposed between a piston mechanism and an anchoring balloon, in accordance with some embodiments of the present invention.

FIG. 23A illustrates an embodiment of a lead extraction device in which a spring is disposed between two portions of the device. In the illustrated embodiment, a spring 2302 is disposed between the proximal anchoring balloon 2304 and piston 2306. Spring 2302 may be bent to provide the lead extraction device with increased flexibility. In some instances, spring 2302 may not be substantially compressed. It should be appreciated that a spring may be introduced between any two portions of a lead extraction device, as the aspects of the present invention are not limited in this respect. Thus, in some embodiments, a spring may be introduced between a piston (e.g., piston 2306) and a distal anchoring balloon in addition to or instead of a spring between a piston and the proximal anchoring balloon. Additionally or alternatively, a spring may be introduced between the distal anchoring balloon and a distal metal tip or cutting portion of the lead extraction device.

Figure 23B:
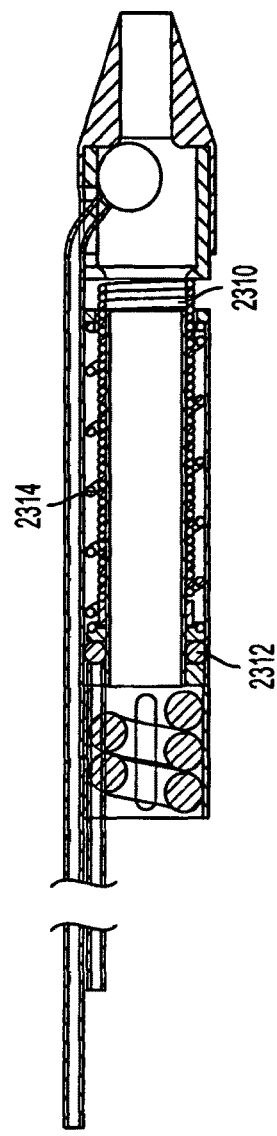
FIGS. 23B-C illustrate a lead extraction device comprising a piston mechanism comprising a flexible portion, in accordance with some embodiments of the present invention.
Figure 23C:
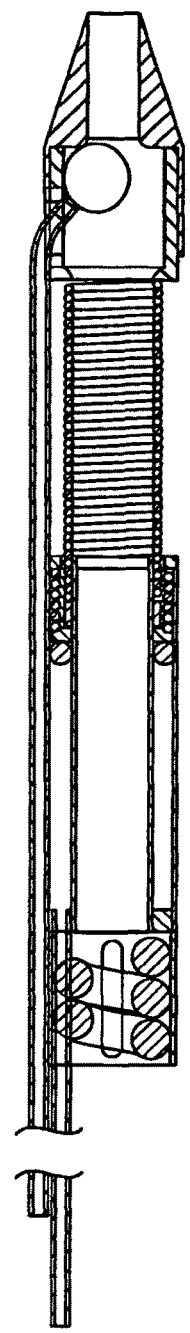

Another approach to make a lead extraction device more flexible includes substituting one or more rigid tubes in the lead extraction device with a corresponding number of springs. For example, as shown in FIGS. 23B and 23C, spring 2310 is attached to an O-ring 2312, which seals piston 2314. Spring 2310 may be bent thereby providing the lead extraction device with increased flexibility. Still in other embodiments, one or more braided tubes and/or one or more plastic tubes may be used in addition to or instead of a spring to provide the lead extraction device with increased flexibility.

As described above, one or more springs may be used to provide a lead extraction device with greater flexibility. In some instances, one or more springs may also be used to connect multiple serial pistons to one another to provide a lead extraction device capable of achieving a higher degree of elongation than a lead extraction device comprising a single piston. Though, it should be recognized that a lead extraction device comprising multiple pistons may be implemented in any other suitable way.

Figure 24A:
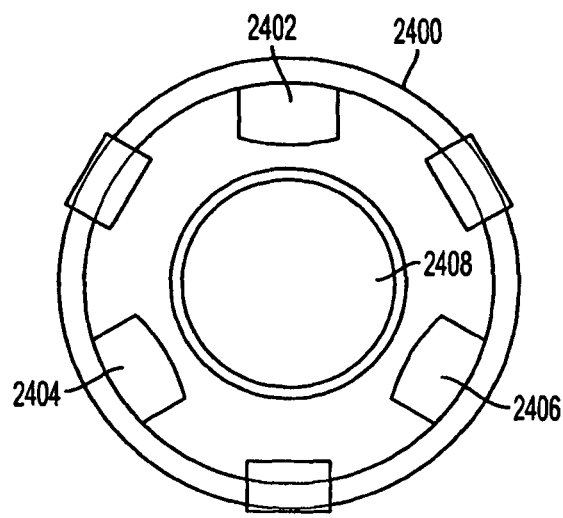
FIGS. 24A-B illustrate an anchoring portion comprising one or more piezoelectric components, in accordance with some embodiments of the present invention.

In some embodiments, one or more piezoelectric components may be used to anchor a lead extraction device to a lead. The piezoelectric component(s) may be used instead of or in addition to components operating based on hydraulic and/or pneumatic principles. Any suitable piezoelectric components may be used including, but not limited to, the piezoelectric components illustrated in FIGS. 24A and 24B. FIG. 24A illustrates a portion 2400 of a lead extraction device comprising piezoelectric components 2402, 2404, and 2406. In the illustrated configuration, components 2402, 2404, and 2406 are not in contact with lead 2408 and, as such, portion 2400 is not anchored to lead 2408. It should be appreciated that three piezoelectric components are shown only as an example and that any suitable number of piezoelectric components may be used as the aspects of the present invention are not limited in this respect.

Figure 24B:
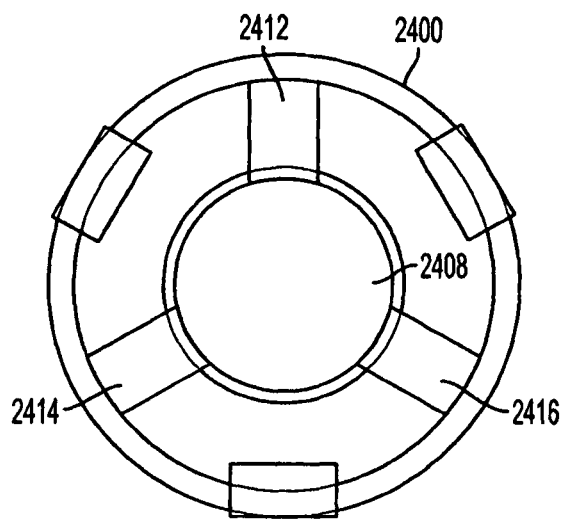

Piezoelectric components may change shape in response to an applied current. For example, as shown in FIG. 24B, piezoelectric components 2402, 2404, and 2406 may change shape by elongating in response to a current being applied resulting in elongated piezoelectric components 2412, 2414, and 2416. As a result of current being applied, friction is created between the elongated piezoelectric components 2412, 2414, and 2416 and lead 2408, thereby anchoring portion 2400 to lead 2408 and, in turn, anchoring a lead extraction device comprising portion 2400 to lead 2408.

Figure 25:
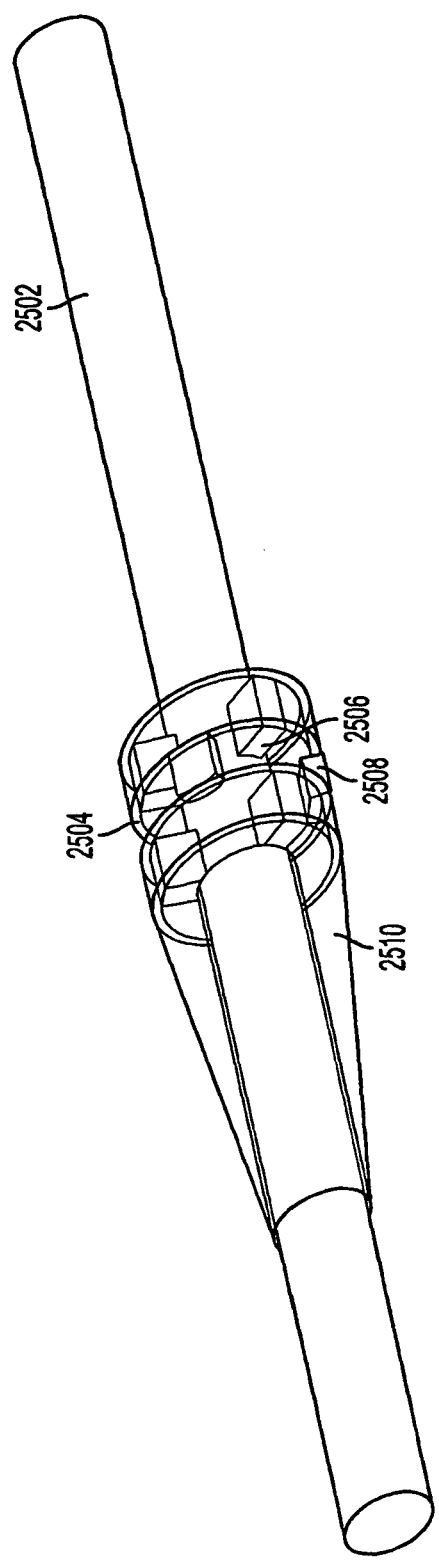
FIG. 25 illustrates a portion of a lead extraction device comprising at least one piezoelectric component illustrated in FIGS. 24A-B, in accordance with some embodiments of the present invention.

Accordingly, in some embodiments, a lead extraction device may comprise one or more anchoring and/or elongation portions comprising one or more piezoelectric components. For example, FIG. 25 shows a lead extraction device 2500 advancing along lead 2502. The lead extraction device comprises a proximal anchoring portion 2504, which includes piezoelectric component 2506. When current is applied to piezoelectric component 2506, component 2506 elongates coming into contact with lead 2502 thereby introducing friction between component 2506 and lead 2502. As a result, proximal anchoring portion 2504 may anchor lead extraction 2500 device to lead 2502.

In the illustrated embodiment, lead extraction device 2500 also comprises an elongation portion that may elongate to advance/rotate cutting portion 2510 along lead 2502. The elongation portion may be implemented in any suitable way and, in some embodiments, may be implemented using one or more piezoelectric components. For example, in the illustrated embodiment, lead extraction device 2500 comprises piezoelectric component 2508, which may elongate in a direction substantially parallel to the direction in which lead extraction device 2500 is advancing. As such, when current is applied to piezoelectric component 2508, this component may elongate advancing a portion of lead extraction device 2500 along lead 2502. Though, it should be recognized that in some embodiments the elongation portion may be comprise one or more hydraulic (e.g., one or more balloons) or pneumatic (e.g., one or more pistons) components instead of or in addition to one or more piezoelectric components (e.g., piezoelectric component 2508) as the aspects of the present invention are not limited in this respect.

It should be recognized that piezoelectric components may be used various ways to anchor a portion of a lead extraction device to a lead and, as such, are not limited to anchoring the portion by coming into contact with the lead upon the application of current, as illustrated in FIGS. 24A, 24B, and 25. For example, in some embodiments, one or more piezoelectric components may be used together with an o-shaped ring to anchor a portion of the lead extraction device to the lead. One such embodiment is illustrated in FIGS. 26A and 26B.

Figure 26A:
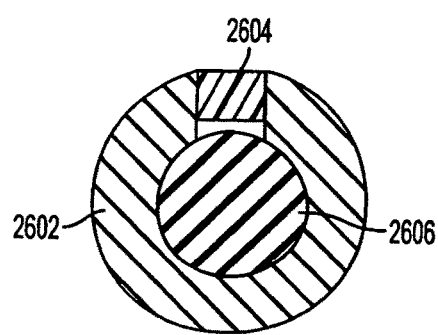
FIGS. 26A-B illustrate views of an anchoring portion comprising a ring and a piezoelectric component, in accordance with some embodiments of the present invention.
Figure 26B:
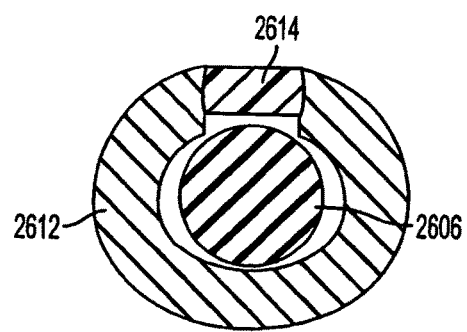

FIG. 26A illustrates an o-shaped ring 2602 and piezoelectric component 2604 surrounding lead 2606. The o-shaped ring 2602 is in contact with lead 2606. Upon the application of current, piezoelectric component 2604 elongates, to form elongated piezoelectric component 2614 shown in FIG. 26B, causing o-shaped ring 2602 to deform and form deformed o-shaped ring 2612. The resulting deformation causes deformed o-shaped ring 2612 to release from lead 2606. Accordingly, shrinking/elongation of the piezoelectric component causes attachment/releasing of the o-shaped ring to the lead. It should be appreciated that in the embodiment illustrated in FIGS. 26A and 26B, the piezoelectric component may elongate in a direction substantially tangential to the surface of the lead, whereas in the embodiment illustrated in FIGS. 24A and 24B, the piezoelectric component may elongate in a direction substantially radial to the surface of the lead.

Piezoelectric components may be also applied to other aspects of the lead extraction process. For example, a steerable guide wire or catheter may be improved by using one or more piezoelectric components. Accordingly, in some embodiments, one or more piezoelectric components may be used within a tip of a guide wire so that the piezoelectric components may be configured to steer the tip of the guide wire. For instance, the piezoelectric components may be disposed within the tip such that, when current is applied to one or more of these piezoelectric components, the shape of these components changes thereby changing the direction in which the guide wire tip is pointing and/or moving. This may aid in steering the guide wire in bifurcations. Any suitable number of piezoelectric components may be disposed in the tip of the guide wire such as at least one, at least two, at least three, at least four, or at least five piezoelectric components.

In some embodiments, a lead extraction device may comprise one or more wheels that rotate to advance the lead extraction device along the lead. Any of numerous types of techniques may be used to rotate the wheels. For example, in some embodiments, electromagnetic techniques may be used to rotate the wheels as described below with reference to FIGS. 27A-27C. Though, it should be recognized that any of numerous other techniques may be used to rotate the wheels.

Figure 27A:
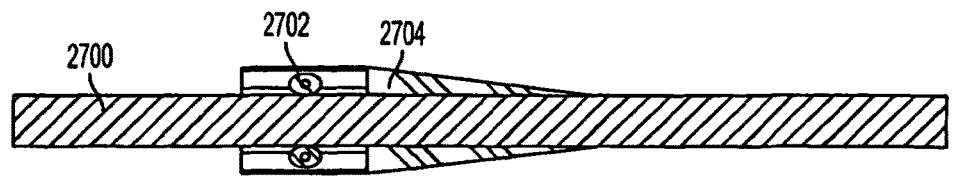
FIGS. 27A-C illustrate views of a lead extraction device comprising rotating wheels, in accordance with some embodiments of the present invention.
Figure 27B:
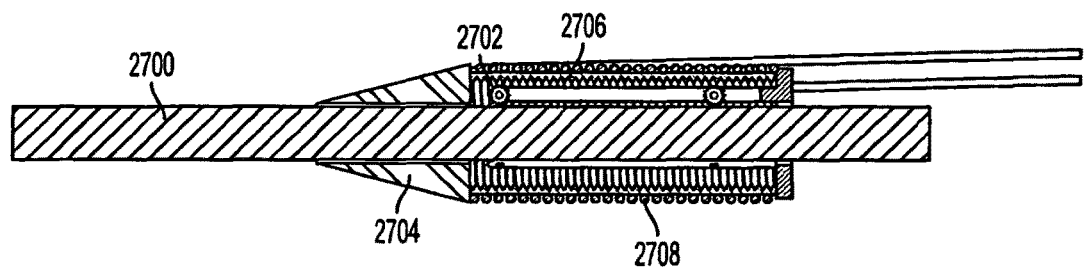
Figure 27C:
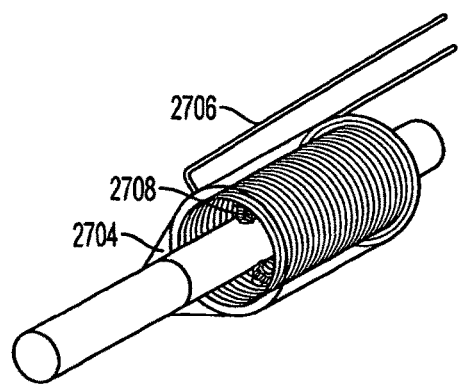

Different views, with varying levels of detail, of an embodiment of a lead extraction device comprising wheels are shown in FIGS. 27A-27C. FIG. 27A shows a side-view of the lead extraction device disposed about lead 2700. The lead extraction device comprises a pair of wheels 2702

(though it should be recognized that a lead extraction device may comprise any suitable number of wheels) that rotate in order to advance cutting portion 2704 along lead 2700.

FIG. 27B shows another side view of the lead-extraction device. As illustrated in FIG. 27B, the lead extraction device comprises a stator 2706 connected to an electric power source. As shown in FIG. 27C, the stator may comprise two wires (though a stator may comprise any suitable number of wires). Flow of electric current through stator 2706 causes rotor 2708, electromagnetically coupled to stator 2706, to rotate. In turn, rotation of the rotor causes gears, which turn wheels 2702, to rotate thereby advancing the lead extraction device along lead 2700. In some embodiments, cutting portion 2704 may rotate when the lead extraction device advances along the lead. In these embodiments, cutting portion 2704 may be bonded to the rotor. In other embodiments, cutting portion 2704 may not rotate when the lead extraction device advances along the lead. In these embodiments, cutting portion 2704 may not be bonded to the rotor.

Another anchoring mechanism, used in some embodiments, comprises a rotational anchoring mechanism. The rotational anchoring mechanism may be configured to twist a spring so as to decrease its inner diameter thereby causing the spring to grip a lead around which the spring is disposed. This may be accomplished in any suitable way. For example, in some embodiments, a rotational anchoring mechanism may comprise one or more mechanical portions, hydraulically or pneumatically actuated, that may be configured to twist the spring so as to decrease its inner diameter. Additionally or alternatively, the rotational anchoring mechanism may comprise one or more piezoelectric components that may be configured to change shape, when current is applied, so as to twist the spring, and decrease its inner diameter.

The inventors have recognized and appreciated that after a lead is extracted from a vein, tissue in the vein that was separated from the lead may partially or fully block that vein. Accordingly, in some embodiments, a lead extraction device may be coupled to a sheath that may keep the vein open after the lead is extracted (e.g., a sheath as described in connection with FIG. 11A). In some instances, the sheath may remain in the vein after the lead is extracted. In these instances, the sheath may serve as a lumen and may aid in the insertion of another lead by keeping the vein open and guiding the lead being inserted away from tissue in the vein. In other instances, the sheath may be removed from the vein when the lead is extracted, but be removed in such a manner so as to reduce tissue blockage following lead removal.

As previously mentioned, in some embodiments, a cutting portion of a lead extraction device may be coupled to component of the device configured to rotate the cutting portion. In some embodiments, the lead extraction device may be coupled to a motor configured to rotate the cutting portion. The motor may be external to the lead extraction device and may rotate the cutting portion using one or more gears and one or more rotating shafts.

Figure 29A:
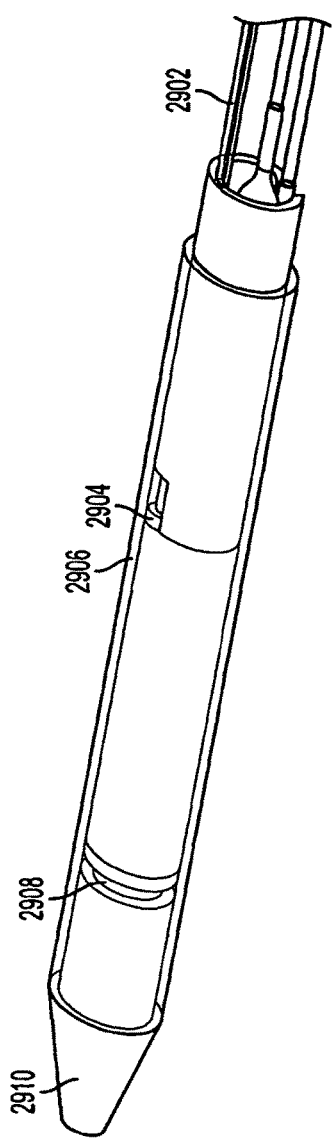
FIGS. 29A-B illustrate views of a lead extraction device comprising a rotating shaft, in accordance with some embodiments of the present invention.
Figure 29B:
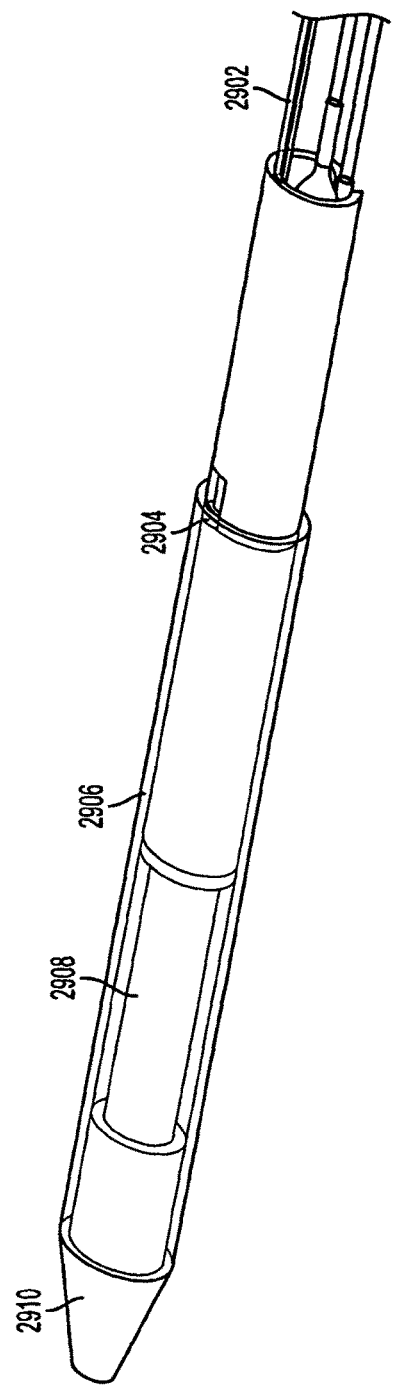
Figure 30A:
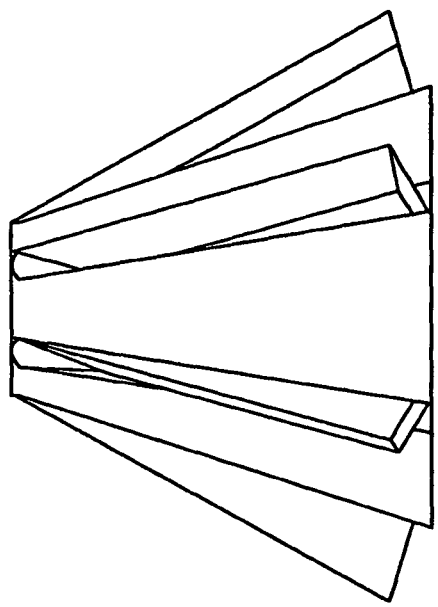
FIGS. 30A-E illustrate views of a cutting portion, in accordance with some embodiments of the present invention.
Figure 30B:
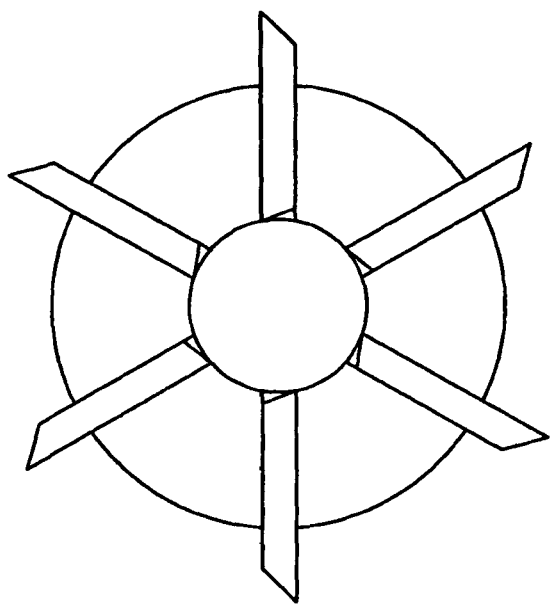
Figure 30C:
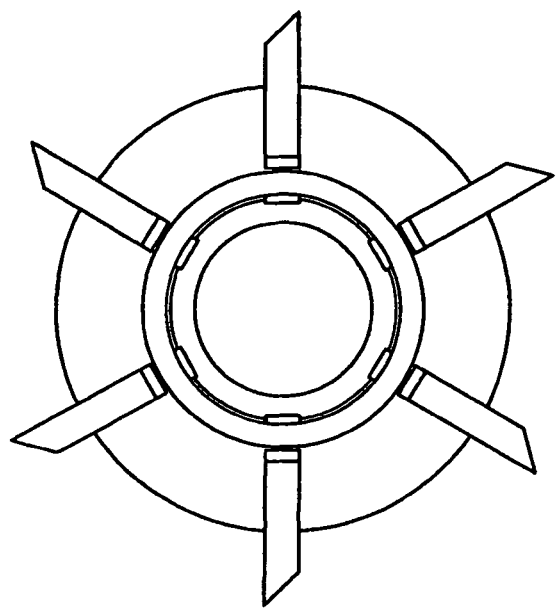
Figure 30D:
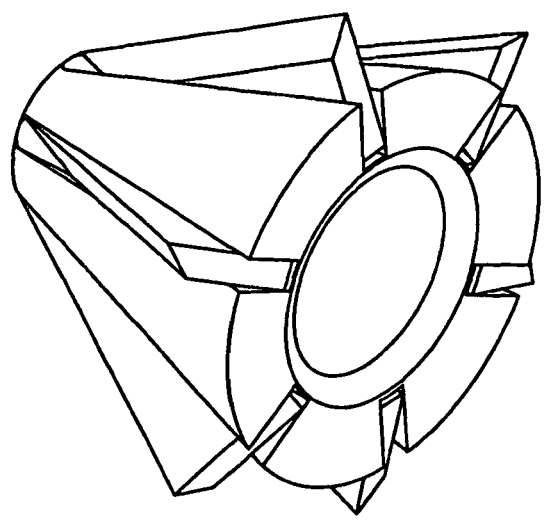
Figure 30E:
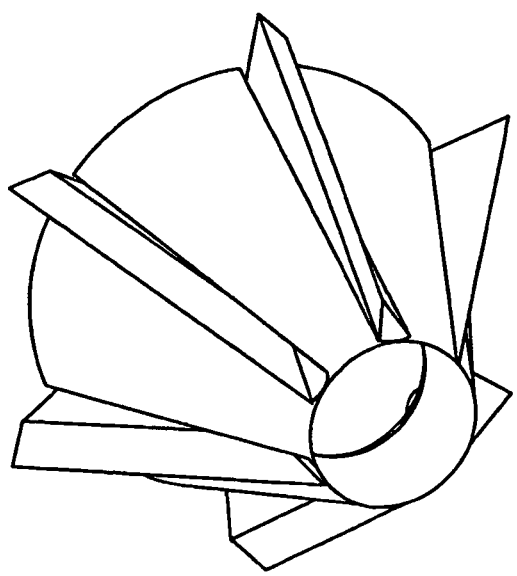

One such embodiment is illustrated in FIGS. 29A and 29B. As shown in FIG. 29A, a lead extraction device comprises a gear 2904 configured to rotate a rotating tube 2906, whose distal end is coupled to cutting portion 2910. The rotating tube comprises an inner portion 2908 that elongates when the rotating tube is rotated, as shown in FIG. 29B. Gear 2904 is coupled to rotating shaft 2902 at its distal end. At its proximal end, rotating shaft 2902 is coupled to a motor configured to rotate rotating shaft 2902. In order to prevent the rotating shaft from damaging any tissue while rotating, the rotating shaft may be surrounded by one or more balloons, tubes, or any other suitable means for preventing the rotating shaft from damaging the vessel.

It should be recognized that any of numerous technologies may be used together with the lead extraction to device to cut and/or separate the tissue from the lead. Such technologies include, but are not limited to, ultrasound technology on the device and/or on the cutting portion, ultrasonic technology on the device and/or on the cutting portion, heat-producing technology on the device and/or on the cutting portion (such technology may include but is not limited to radio-frequency based heat-producing technology), laser-based technology on the device and/or the cutting portion, and any cutting portion shaped in accordance with one or more of the illustrations shown in FIGS. 30A-30E.

In some embodiments, where a lead extraction device comprises one or more springs, the lead extraction device may further comprise one or more portions configured to prevent tissue contact with the spring(s). Such portions may prevent tissue being stuck between the coils of the spring(s) as the spring(s) expand and relax. In some embodiments, such as those illustrated in FIGS. 31A and 31B, a spring may be enveloped in a tube to prevent tissue contact with the spring.

Similarly, in some embodiments, where a lead extraction device comprises one or more pistons, the lead extraction device may further comprise one or more portions configured to prevent tissue contact with the piston(s). Such portions may prevent tissue recoil during operation of the piston. In some instances, such portions may further keep a blood vessel open after the lead is extracted. In some embodiments, one or more balloons may be used to envelop the piston(s) to prevent tissue contact with the piston(s). Such balloons may be inflated outward on in any other suitable way to prevent tissue contact with the piston(s). Any of numerous types of balloons may be used including, but not limited to, balloons used for percutaneous transluminal coronary angioplasty and their variants.

The above-described embodiments of the present invention can be implemented in any of numerous ways, and the examples described herein are not limiting. In addition, various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. In particular, the various concepts relating to anchoring, advancing, cutting, and controlling may be implemented in any way and be used alone or in any combination. In addition, embodiments of a tool may be operated manually (e.g., by a surgeon) or automatically (e.g., using a control unit), or may be operated using any combination of manual and automatic techniques such that some aspects of the operation are manual, and others are automatic. The invention is capable of other embodiments and of being practiced or of being carried out in various ways.

The various processes outlined herein may be coded as software that is executable on one or more processors that employ any one of a variety of operating systems or platforms. Additionally, such software may be written using any of numerous suitable programming languages and/or programming or scripting tools, and also may be compiled as executable machine language code or intermediate code that is executed on a virtual machine or a suitable framework. In this respect, various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, implement the various embodiments of the present invention. The non-transitory computer-readable medium or media may be transportable, such that the program or programs stored thereon may be loaded onto any computer resource to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion among different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term). The phraseology and terminology used herein is for the purpose of description and should not be regarded as limiting. The use of "including," "comprising," "having," "containing", "involving", and variations thereof, is meant to encompass the items listed thereafter and additional items.

What is claimed is:

1. A system for assisting in removing an implanted lead, the system comprising:
   a device for separating tissue from the lead, the device comprising:
      a body having a proximal portion and a distal portion, the body adapted to accommodate the lead;
      at least one expansion component capable of increasing a distance between the proximal portion and the distal portion at least in part by fluid pressure applied to the at least one expansion component;
      a separating component coupled to the at least one expansion component such that when fluid pressure is applied to the at least one expansion component, the separating component is forced in a forward direction along the lead to assist in separating tissue from the lead;

at least one proximal anchoring component capable of providing pressure on the lead that resists movement of at least part of the proximal portion along the lead at least in part by fluid pressure applied to the at least one proximal anchoring component to provide an anchor for the separating component to assist in separating tissue from the lead; and at least one distal anchoring component capable of providing pressure on the lead that resists movement of at least part of the distal portion along the lead at least in part by fluid pressure applied to the at least one distal anchoring component; and a control unit configured to operate the device, the control unit comprising at least one controller configured to cause fluid pressure to be applied to the at least one proximal anchoring component, the at least one expansion component, and the at least one distal anchoring component in a predetermined sequence.

2. The system of claim 1, wherein the at least one controller is configured to cause fluid pressure to be released from the at least one expansion component, the at least one proximal anchoring component and the at least one distal anchoring component in a predetermined sequence.

3. The system of claim 2, wherein the at least one controller is configured to control the device by sequentially applying fluid pressure to the proximal anchoring component, applying fluid pressure to the expansion component, applying fluid pressure to the distal anchoring component, releasing fluid pressure from the proximal anchoring component, releasing fluid pressure from the expansion component, and releasing fluid pressure from the distal anchoring component.

4. The system of claim 3, wherein the at least one controller is configured to repeat the sequence of applying fluid pressure to the proximal anchoring component, applying fluid pressure to the expansion component, applying fluid pressure to the distal anchoring component, releasing fluid pressure from the proximal anchoring component, releasing fluid pressure from the expansion component, and releasing fluid pressure from the distal anchoring component to separate tissue adhered to the lead.

5. The system of claim 3, wherein the control unit comprises a plurality of valves and wherein the at least one controller is configured to operate the plurality of valves to apply and/or release fluid pressure from the at least one proximal anchoring component, the at least one expansion component, and the at least one distal anchoring component in the predetermined sequence.

6. The system of claim 1, further comprising a first inflation tube through which fluid is applied to the at least one proximal anchoring component, a second inflation tube through which fluid is applied to the at least one expansion component, and a third inflation tube through which fluid is applied to the at least one distal anchoring component so that the at least one proximal anchoring component, the at least one expansion component and the at least one distal anchoring component are configured to be operated independently.

7. The system of claim 1, wherein the control unit comprises an input mechanism that allows a user to start and/or stop operation of the device.

8. The system of claim 1, wherein the at least one expansion component comprises a piston mechanism having a piston arranged to slide forward and backward in an axial direction with respect to the body, wherein the piston is forced in a forward direction along the lead when fluid pressure is applied to the piston mechanism.

9. The system of claim 1, wherein the device comprises a spring mechanism coupled between the proximal portion and the distal portion, wherein the spring mechanism is stretched when fluid pressure is applied to the piston mechanism and contracts to advance the proximal portion when fluid pressure is released from the at least one expansion component and the at least one proximal anchoring component.

10. The system of claim 1, wherein the at least one distal anchoring component, when fluid pressure is applied to the at least one distal anchoring component, causes gripping contact on a full circumference of a portion of the lead.

11. The system of claim 1, wherein the at least one proximal anchoring component, when fluid pressure is applied to the at least one proximal anchoring component, causes gripping contact on a full circumference of a portion of the lead.

12. The system of claim 1, wherein the at least one distal anchoring component comprises at least one anchoring balloon that provides pressure on the lead that resists movement of the distal portion along the lead when inflated.

13. The system of claim 1, wherein the at least one proximal anchoring component includes at least one anchoring balloon that provides pressure on the lead to resist movement of the proximal portion along the lead when inflated.

14. The system of claim 1, wherein the device comprises a rotating component coupled to the separating component and the at least one expansion component, wherein when fluid pressure is applied to the at least one expansion component, force from the at least one expansion component causes the rotating component to rotate the separating component while the separating component is being forced in the forward direction along the lead to assist in separating tissue from the lead.

* * * * *